(12) United States Patent
Onji

(10) Patent No.: US 11,147,449 B2
(45) Date of Patent: Oct. 19, 2021

(54) OPHTHALMOLOGICAL DEVICE

(71) Applicant: TOPCON CORPORATION, Tokyo (JP)

(72) Inventor: Hirokazu Onji, Itabashi-ku (JP)

(73) Assignee: TOPCON CORPORATION, Tokyo (JP)

( * ) Notice: Subject to any disclaimer, the term of this patent is extended or adjusted under 35 U.S.C. 154(b) by 242 days.

(21) Appl. No.: 16/608,209

(22) PCT Filed: Feb. 7, 2018

(86) PCT No.: PCT/JP2018/004192
§ 371 (c)(1),
(2) Date: Oct. 25, 2019

(87) PCT Pub. No.: WO2018/198474
PCT Pub. Date: Nov. 1, 2018

(65) Prior Publication Data
US 2021/0093191 A1    Apr. 1, 2021

(30) Foreign Application Priority Data

Apr. 26, 2017   (JP) .............................. JP2017-087259

(51) Int. Cl.
*A61B 3/12* (2006.01)
*A61B 3/00* (2006.01)
*A61B 3/10* (2006.01)

(52) U.S. Cl.
CPC .............. *A61B 3/12* (2013.01); *A61B 3/0058* (2013.01); *A61B 3/102* (2013.01)

(58) Field of Classification Search
CPC ......... A61B 3/12; A61B 3/0058; A61B 3/102; A61B 3/0041; A61B 3/0025;

(Continued)

(56) References Cited

U.S. PATENT DOCUMENTS

2012/0051611 A1    3/2012 Takama
2014/0221827 A1*   8/2014 Motaghiannezam ....................... A61B 3/0025
600/425

(Continued)

FOREIGN PATENT DOCUMENTS

CN    102397055 A    4/2012
CN    105682538 A    6/2016

(Continued)

OTHER PUBLICATIONS

International Search Report and Written Opinion dated Apr. 24, 2018 for PCT/JP2018/004192 filed on Feb. 7, 2018, 11 pages including English Translation of the International Search Report.

(Continued)

*Primary Examiner* — Mohammed A Hasan
(74) *Attorney, Agent, or Firm* — Xsensus LLP

(57) ABSTRACT

In an ophthalmological device, a memory stores a three dimensional data set acquired by applying OCT to a subject's eye. A fourth color coding unit assigns color information according to a depth position to the three dimensional data set. A fourth layer region identifying unit identifies layer regions by applying segmentation to the three dimensional data set, A fourth blood vessel region extracting unit extracts a blood vessel region from each of the layer regions identified. A fourth front image constructing unit constructs a front image based on each of the blood vessel regions extracted. A fourth image composing unit composes at least two of the front images constructed based on the color information, to construct a composite front image.

20 Claims, 15 Drawing Sheets

(58) Field of Classification Search
CPC ........ A61B 3/1233; G06T 2207/30041; G06T 2207/10028; G06T 2207/10101; G06T 7/11; G06T 11/60
USPC .......................................................... 351/206
See application file for complete search history.

(56) References Cited

U.S. PATENT DOCUMENTS

| | | |
|---|---|---|
| 2017/0065170 A1 | 3/2017 | Yamashita |
| 2018/0116501 A1 | 5/2018 | Akiba et al. |
| 2018/0360308 A1 | 12/2018 | Aimi et al. |

FOREIGN PATENT DOCUMENTS

| | | | |
|---|---|---|---|
| DE | 112017000663 T5 * | 10/2018 | ............. A61B 3/103 |
| EP | 3387984 A1 | 10/2018 | |
| JP | 2016-198447 A | 12/2016 | |
| JP | 2017-047111 A | 3/2017 | |

OTHER PUBLICATIONS

Choi, W. J., et al., "Improved microcirculation imaging of human skin in vino using optical microangiography with a correlation mapping mask", Journal of Biomedical Optics, vol. 19, No. 3, Mar. 12, 2014, pp. 036010-1 to 036010-9.

Daniel, M. S., et al., "Phase-Variance Optical Coherence Tomography: A Technique for Noninvasive Angiography," American Academy of Ophthalmology, Ophthalmology vol. 121, No. 1, Jan. 2014, pp. 180-187.

Mahmud, S. M., et al., "Review of speckle and phase variance optical coherence tomography to visualize microvascular networks," Journal of Biomedical Optics, vol. 18, No. 5, Apr. 24, 2013, pp. 050901-1 to 050901-13.

Zhang, Q. Q., et al., "Wide-field imaging of 1-13 retinal vasculature using optical coherence tomography-based microangiography provided by motion tracking," Journal of Biomedical Optics, vol. 20, No. 6, Jun. 23, 2015, pp. 066008-1 to 066008-9.

Extended European search report dated Dec. 22, 2020, in corresponding European patent Application No. 18791207.6, 7 pages.

Chinese Office Action dated Jun. 3, 2021, in corresponding Chinese Patent Application No. 201880026689.1.

* cited by examiner

OPHTHALMOLOGICAL DEVICE

CROSS-REFERENCE TO RELATED APPLICATIONS

This application is a national stage (under 35 U.S.C. 371) of International Patent Application No. PCT/JP2018/004192, filed Feb. 7, 2018 claiming priority to Japanese Patent Application No. 2017-087259, filed. Apr. 26, 2017, both of which are herein incorporated by reference in their entirety.

FIELD

The present disclosure relates generally to an ophthalmological device.

BACKGROUND

Diagnostic imaging serves an important role in the field of ophthalmology. In recent years, utilization of optical coherence tomography (OCT) has advanced. OCT is being used not only for acquisition of B-scan images and three dimensional images of a subject's eye but also for acquisition of front images (en face images) such as C-scan images and shadowgrams. OCT is also utilized for acquisition of images in which a specific site of the subject's eye is emphasized, and for acquisition of functional information. For example, B-scan images and/or front images in which blood vessels such as retinal blood vessels and/or choroidal blood vessels are emphasized can be constructed based on time-series volume data acquired using OCT. Such images are referred to as blood vessel enhanced images, blood vessel emphasized images, or angiograms. Furthermore, rendering techniques and graphical user interfaces (GUIs) for observing a desired slice of the subject's eye have been proposed.

PATENT DOCUMENT 1: Japanese Unexamined Patent Application Publication No. 2016-198447

NON-PATENT DOCUMENT 1: Daniel M. Schwarz et al., "Phase-Variance Optical Coherence Tomography: A Technique for Noninvasive Angiography", Ophthalmology Vol. 121, Number 1, January 2014

Non-Patent Document 1 discloses a technique for performing color coding on a plurality of blood vessel emphasized images in mutually different depth ranges and composing and displaying the color-coded images. However, non-blood-vessel tissues are also depicted in the blood vessel emphasized images, and therefore difficulty exists in clearly recognizing or detecting the three dimensional distribution of blood vessels from the color-coded composite image.

An object of the present disclosure is to clearly grasp the three dimensional distribution of ocular blood vessels.

The first aspect of exemplary embodiments is an ophthalmological device that includes the following elements: a memory that stores a three dimensional data set acquired by applying optical coherence tomography to a subject's eye; a first blood vessel region extracting unit that extracts a blood vessel region from the three dimensional data set; a first layer region identifying unit that identifies a plurality of layer regions by applying segmentation to the three dimensional data set; a first common region identifying unit that identifies a common region between the blood vessel region and a layer region, for each of the plurality of layer regions; a first front image constructing unit that constructs a front image based on each of a plurality of common regions identified by the first common region identifying unit; a first color coding unit that assigns mutually different color information to a plurality of front images constructed by the first front image constructing unit; and a first image composing unit that composes at least two of the plurality of front images to which the color information has been assigned, to construct a composite front image.

The second aspect of exemplary embodiments is an ophthalmological device that includes the following elements: a memory that stores a three dimensional data set acquired by applying optical coherence tomography to a subject's eye; a second layer region identifying unit that identifies a plurality of layer regions by applying segmentation to the three dimensional data set; a second blood vessel region extracting unit that extracts a blood vessel region from each of the plurality of layer regions; a second front image constructing unit that constructs a front image based on each of a plurality of blood vessel regions extracted by the second blood vessel region extracting unit; a second color coding unit that assigns mutually different color information to a plurality of front images constructed by the second front image constructing unit; and a second image composing unit that composes at least two of the plurality of front images to which the color information has been assigned, to construct a composite front image.

The third aspect of exemplary embodiments is an ophthalmological device that includes the following elements: a memory that stores a three dimensional data set acquired by applying optical coherence tomography to a subject's eye; a third color coding unit that assigns color information according to a depth position to the three dimensional data set; a third blood vessel region extracting unit that extracts a blood vessel region from the three dimensional data set; a third layer region identifying unit that identifies a plurality of layer regions by applying segmentation to the three dimensional data set; a third common region identifying unit that identifies a common region between the blood vessel region and a layer region, for each of the plurality of layer regions; a third front image constructing unit that constructs a front image based on each of a plurality of common regions identified by the third common region identifying unit; and a third image composing unit that composes at least two of a plurality of front images constructed by the third front image constructing unit based on the color information, to construct a composite front image.

The fourth aspect of exemplary embodiments is an ophthalmological device that includes the following elements: a memory that stores a three dimensional data set acquired by applying optical coherence tomography to a subject's eye; a fourth color coding unit that assigns color information according to a depth position to the three dimensional data set; a fourth layer region identifying unit that identifies a plurality of layer regions by applying segmentation to the three dimensional data set; a fourth blood vessel region extracting unit that extracts a blood vessel region from each of the plurality of layer regions; a fourth front image constructing unit that constructs a front image based on each of a plurality of blood vessel regions extracted by the fourth blood vessel region extracting unit; and a fourth image composing unit that composes at least two of a plurality of front images constructed by the fourth front image constructing unit based on the color information, to construct a composite front image.

The fifth aspect of exemplary embodiments is an ophthalmological device that includes the following elements: a memory that stores a three dimensional data set acquired by applying optical coherence tomography to a subject's eye; a fifth color coding unit that assigns color information according to a depth position to the three dimensional data set; a fifth blood vessel region extracting unit that extracts a blood vessel region from the three dimensional data set; a fifth layer region identifying unit that identifies a plurality of layer regions by applying segmentation to the three dimensional data set; a fifth common region identifying unit that identifies a common region between the blood vessel region and a layer region, for each of the plurality of layer regions; a fifth front image constructing unit that constructs a front image based on the color information and a common region, for each of a plurality of common regions identified by the fifth common region identifying unit; and a fifth image composing unit that composes at least two of a plurality of front images constructed by the fifth front image constructing unit, to construct a composite front image.

The sixth aspect of exemplary embodiments is an ophthalmological device that includes the following elements: a memory that stores a three dimensional data set acquired by applying optical coherence tomography to a subject's eye; a sixth color coding unit that assigns color information according to a depth position to the three dimensional data set; a sixth layer region identifying unit that identifies a plurality of layer regions by applying segmentation to the three dimensional data set; a sixth blood vessel region extracting unit that extracts a blood vessel region from each of the plurality of layer regions; a sixth front image constructing unit that constructs a front image based on the color information and a blood vessel region, for each of a plurality of blood vessel regions extracted by the sixth blood vessel region extracting unit; and a sixth image composing unit that composes at least two of a plurality of front images constructed by the sixth front image constructing unit, to construct a composite front image.

The seventh aspect of exemplary embodiments is an ophthalmological device that includes the following elements: a memory that stores a three dimensional data set acquired by applying optical coherence tomography to a subject's eye; a seventh blood vessel region extracting unit that extracts a blood vessel region from the three dimensional data set; a seventh layer region identifying unit that identifies a plurality of layer regions by applying segmentation to the three dimensional data set; a seventh color coding unit that assigns mutually different color information to the plurality of layer regions; a seventh common region identifying unit that identifies a common region between the blood vessel region and a layer region, for each of the plurality of layer regions; a seventh front image constructing unit that constructs a front image based on the color information and a common region, for each of a plurality of common regions identified by the seventh common region identifying unit; and a seventh image composing unit that composes at least two of a plurality of front images constructed by the seventh front image constructing unit, to construct a composite front image.

The eighth aspect of exemplary embodiments is an ophthalmological device that includes the following elements: a memory that stores a three dimensional data set acquired by applying optical coherence tomography to a subject's eye; an eighth layer region identifying unit that identifies a plurality of layer regions by applying segmentation to the three dimensional data set; an eighth color coding unit that assigns mutually different color information to the plurality of layer regions; an eighth blood vessel region extracting unit that extracts a blood vessel region from each of the plurality of layer regions; an eighth front image constructing unit that constructs a front image based on the color information and a blood vessel region, for each of a plurality of blood vessel regions extracted by the eighth blood vessel region extracting unit; and an eighth image composing unit that composes at least two of a plurality of front images constructed by the eighth front image constructing unit, to construct a composite front image.

The ninth aspect of exemplary embodiments is an ophthalmological device that includes the following elements: a memory that stores a three dimensional data set acquired by applying optical coherence tomography to a subject's eye; a ninth layer region identifying unit that identifies a plurality of layer regions by applying segmentation to the three dimensional data set; a ninth front image constructing unit that constructs a front image based on each of the plurality of layer regions; a ninth blood vessel region extracting unit that extracts a blood vessel region from each of a plurality of front images constructed by the ninth front image constructing unit; a ninth color coding unit that assigns mutually different color information to a plurality of blood vessel regions extracted by the ninth blood vessel region extracting unit; and a ninth image composing unit that composes at least two of the plurality of blood vessel regions to which the color information has been assigned, to construct a composite front image.

The tenth aspect of exemplary embodiments is the ophthalmological device of any of the first to ninth aspects that further includes a display controller configured to display the composite front image on a display device based on the color information.

The eleventh aspect of exemplary embodiments is the ophthalmological device of the tenth aspect that further includes an operation unit configured to receive an operation for selecting two or more front images from among the plurality of front images. In addition, the display controller is configured to display a composite front image constructed based on the two or more front images selected using the operation unit, on the display device.

The twelfth aspect of exemplary embodiments is the ophthalmological device of the eleventh aspect that further includes an interested blood vessel region setting unit configured to set an interested blood vessel region in the blood vessel region. In addition, the display controller is configured to display a composite image of the composite front image constructed based on the two or more front images and the interested blood vessel region in a front image different from the two or more front images from among the plurality of front images, on the display device.

The thirteenth aspect of exemplary embodiments is the ophthalmological device of any of the first to twelfth aspects that further includes a data set acquiring unit configured to acquire a three dimensional data set by applying optical coherence tomography to a subject's eye. In addition, the memory is configured to store the three dimensional data set acquired by the data set acquiring unit.

According to some exemplary aspects, the three dimensional distribution of ocular blood vessels can be clearly grasped.

DETAILED DESCRIPTION OF THE EMBODIMENTS

Figure 1:
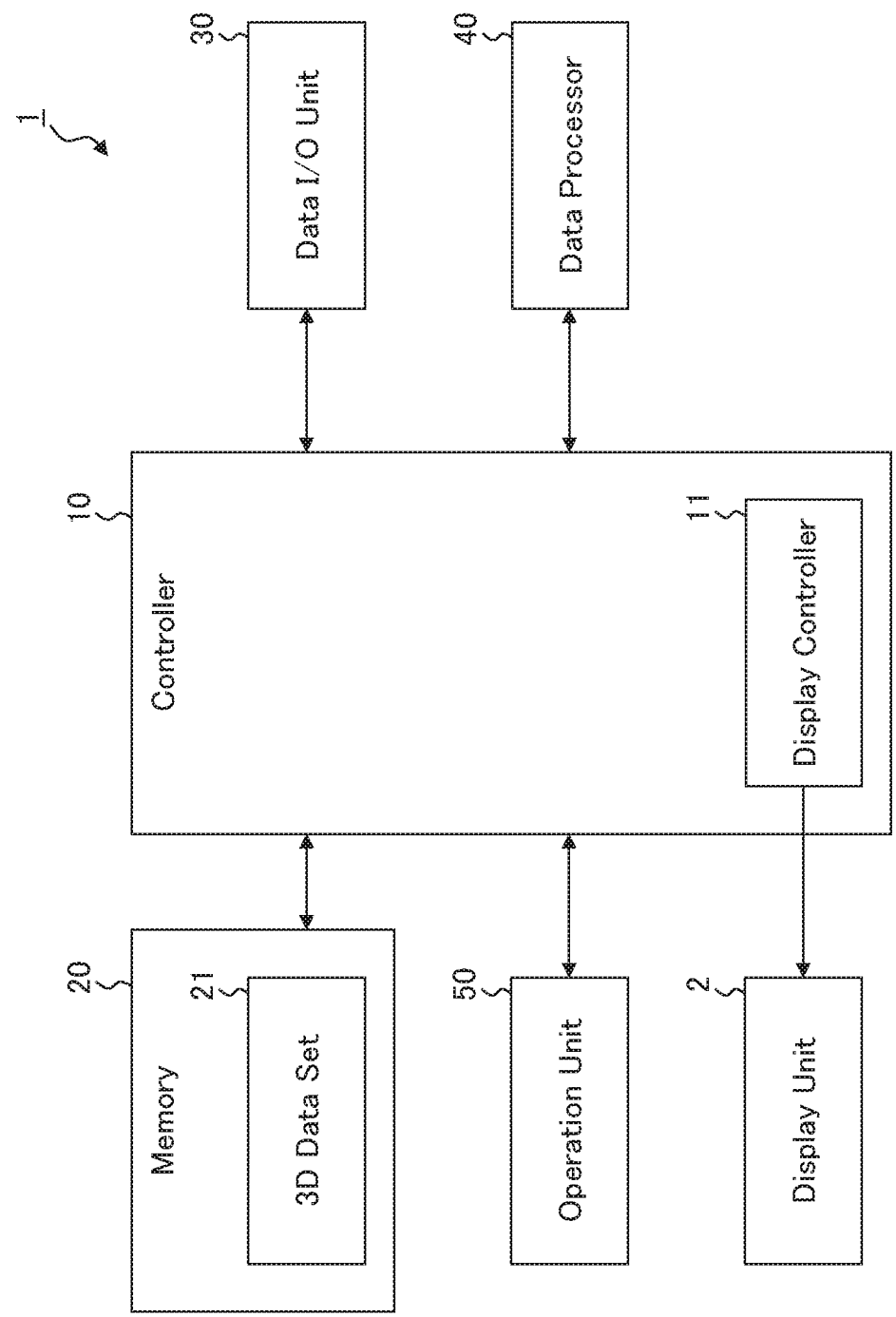
FIG. 1 is a schematic diagram illustrating an example of the configuration of the ophthalmological device according to the exemplary embodiment.

Some exemplary embodiments of the present invention will be described with referring to the drawings. In addition, any contents of the documents cited in the present specification and any existing techniques and technologies may be incorporated in the embodiments.

Embodiments provide an image of the subject's eye. The image is a blood vessel emphasized image (i.e., angiogram) that is constructed on the basis of a three dimensional data set composed of a plurality of two dimensional data sets obtained by repeatedly scanning substantially the same area of the subject's eye. The three dimensional data set is obtained, for example, by performing the following steps: a step of scanning each of a plurality of B cross sections B1, B2, . . . , Bn, a predetermined number of times (e.g., four times each); a step of constructing a predetermined number of B-scan images for each B cross section Bi (i=1, 2, . . . , N); and a step of embedding these B-scan images in the same three dimensional coordinate system. In addition, a step of applying voxelization to the B-scan images may optionally be included. Such an image constructing technique is known.

First Embodiment

The ophthalmological device according to the first embodiment will be described. The ophthalmological device 1 illustrated in FIG. 1 is configured to display various kinds of information such as images of the subject's eye on the display unit 2. The display unit 2 may be a part of the ophthalmological device 1 or may be an external device connected to the ophthalmological device 1.

The ophthalmological device 1 includes the controller 10, the memory 20, the data input and output (I/O) unit 30, the data processor 40, and the operation unit 50.

(Controller 10)

The controller 10 controls each part of the ophthalmological device 1. The controller 10 includes a processor. In the present specification, the term "processor" is used to mean, for example, a circuit such as a central processing unit (CPU), a graphics processing unit (GPU), an application specific integrated circuit (ASIC), a programmable logic device (e.g., a simple programmable logic device (SPLD), a complex programmable logic device (CPLD), a field programmable gate array (FPGA)), or the like. The controller 10 realizes the functions according to the embodiment, for example, by reading out and executing a program(s) stored in a storage circuit or a storage device (e.g., the memory 20).

The controller 10 includes the display controller 11. The display controller 11 executes control for displaying information on the display unit 2.

(Memory 20)

The memory 20 stores various kinds of information. In the present example, the memory 20 stores the three dimensional data set 21 acquired by applying OCT scanning to the subject's eye. The memory 20 includes a storage device such as a hard disk drive.

Although not shown in the drawings, the memory 20 stores templates of screens, dialogs, icons, and other types of objects, which are displayed as GUI on the display unit 2. The memory 20 stores a program executed for processing image data and a program executed for controlling the GUI. The processing according to the embodiment is realized by the cooperation of software including such programs and hardware including one or more processors.

(Data Input and Output Unit 30)

The data input and output unit 30 performs input of data into the ophthalmological device 1 and output of data from the ophthalmological device 1. The data input and output unit 30 may be configured to perform either one of data input or data output only. The data input and output unit 30 may include a communication device for performing data transmission and data reception via a communication line such as a local area network (LAN), the Internet, a dedicated line, etc. The data input and output unit 30 may include a reader writer device for reading data from a recording medium and writing data into a recording medium. Further, the data input and output unit 30 may include an image scanner that scans information recorded on a print medium or the like, a printer that records information on a paper medium, or other types of devices.

(Data Processor 40)

The data processor 40 includes a processor and executes various kinds of data processing. For example, the data processor 40 applies image processing to ophthalmic image data. As a typical example, the data processor 40 may perform rendering such as three dimensional computer graphics (3DCG).

When a three dimensional data set (e.g., volume data, stack data) acquired by a three dimensional OCT scan (volume scan) of the subject's eye has been input to the ophthalmological device 1, the data processor 40 may apply various kinds of rendering to the three dimensional data set to generate a B-scan image (longitudinal cross sectional image, axial cross sectional image), a C-scan image (transverse cross sectional image, horizontal cross sectional image), a projection image, a shadowgram, or other types of images. An image of an arbitrarily-designated cross section such as a B-scan image or a C-scan image is constructed by, for example, selecting image elements (pixels, voxels) on the designated cross section from the three dimensional data set. A projection image is constructed by projecting (integrating) the three dimensional data set in a predetermined direction. Here, the projection direction may be the Z direction (depth direction, axial direction). A shadowgram is constructed by projecting (integrating) a part of the three dimensional data set in a predetermined direction. Here, the part projected is, for example, partial data of the three dimensional data set corresponding to a specific layer. An image that is viewed from the front side of the subject's eye, such as a C-scan image, a projection image, or a shadowgram, is referred to as a front image or an en face image.

The data processor 40 is capable of executing various kinds of image processing in addition to rendering. For example, the data processor 40 may be configured to perform segmentation and size analysis. Segmentation is image processing for determining (identifying, specifying) a specific tissue or a specific tissue boundary. Size analysis is image processing for determining (calculating) the size of a specific tissue. The size of a tissue is, for example, layer thickness or volume. In the event that a specific layer (or a specific layer boundary) is identified by segmentation, a B-scan image or a front image can be reconstructed so that the specific layer becomes flat. Such an image is referred to as a flattened image.

(On Blood Vessel Emphasized Images)

Examples of images displayed by the ophthalmological device 1 include blood vessel emphasized images (angiograms). A blood vessel emphasized image is an image constructed by analyzing OCT data to identify image regions corresponding to blood vessels (referred to as blood vessel regions), and changing the representation aspects of the identified blood vessel regions to emphasize the blood vessel regions. The identification of the blood vessel regions is performed using a plurality of pieces of OCT data acquired by repeatedly applying OCT scanning to substantially the same area of the subject's eye. In some embodiments, a three dimensional data set is used to display a blood vessel emphasized image as a front image (referred to as a blood vessel emphasized front image). Such a three dimensional data set is stored in the memory 20 (the three dimensional data set 21 illustrated in FIG. 1).

There are several types of methods for constructing blood vessel emphasized images. A typical example thereof is described herein. Note that one or more parts or all of the plurality of steps included in the method described below may be performed by the data processor 40. In addition or instead, one or more parts or all of the plurality of steps included in the method described below may be performed by another device (e.g., a computer, an ophthalmological device, or the like).

To begin with, repetitive scanning (iterative scanning) is applied to each of a plurality of B cross sections of the subject's eye to create a three dimensional data set in which a plurality of B-scan images arranged in time series (along the time axis) is assigned to each B cross section. Fixation and tracking are known as methods for repeatedly scanning substantially the same B cross section. The three dimensional data set at this stage may be stored in the memory 20 as the three dimensional data set 21.

Next, position matching (registration) of the plurality of B-scan images is performed for each B cross section. The position matching is performed, for example, by using any known image matching technique. A typical example thereof may execute extraction of a feature region from each B-scan image, and position matching of the plurality of B-scan images via position matching of the plurality of extracted feature regions. The three dimensional data set at this stage may be stored in the memory 20 as the three dimensional data set 21.

Subsequently, a process of identifying image regions that change between the plurality of B-scan images to which the registration have been applied is performed. This processing includes, for example, a process of determining the difference between different B-scan images. Each B-scan image is brightness image data representing the morphology (structure) of the subject's eye, and it can be considered that an image region therein corresponding to a non-blood-vessel site is substantially invariant. On the other hand, considering a phenomenon that the backscattering contributing to interference signals randomly varies under the influence of blood flow, an image region in which a change has occurred between the plurality of B-scan images aligned can be regarded as a blood vessel region. Here, the image region with the change includes, for example, pixels with non-zero difference or pixels with difference equal to or larger than a predetermined threshold. The three dimensional data set at this stage may be stored in the memory 20 as the three dimensional data set 21.

To the image region identified in this way, information indicating that the image region is a blood vessel region can be assigned. With this, the pixel values of the blood vessel region can be changed and emphasized (highlighted) when displaying a blood vessel emphasized image as a B-scan image or a blood vessel emphasized front image. The three dimensional data set at this stage may be stored in the memory 20 as the three dimensional data set 21.

The detailed configuration of the data processor 40 will be described later.

(Operation Unit 50)

The operation unit 50 is used by the user to input instructions and information to the ophthalmological device 1. The operation unit 50 may include any types of known operation devices usable together with a computer. For example, the operation unit 50 may include a pointing device such as a mouse, a touch pad, or a track ball. The operation unit 50 may include a keyboard, a pen tablet, a dedicated operation panel, or other devices.

(Configuration Examples of the Data Processor 40)

Figure 2:
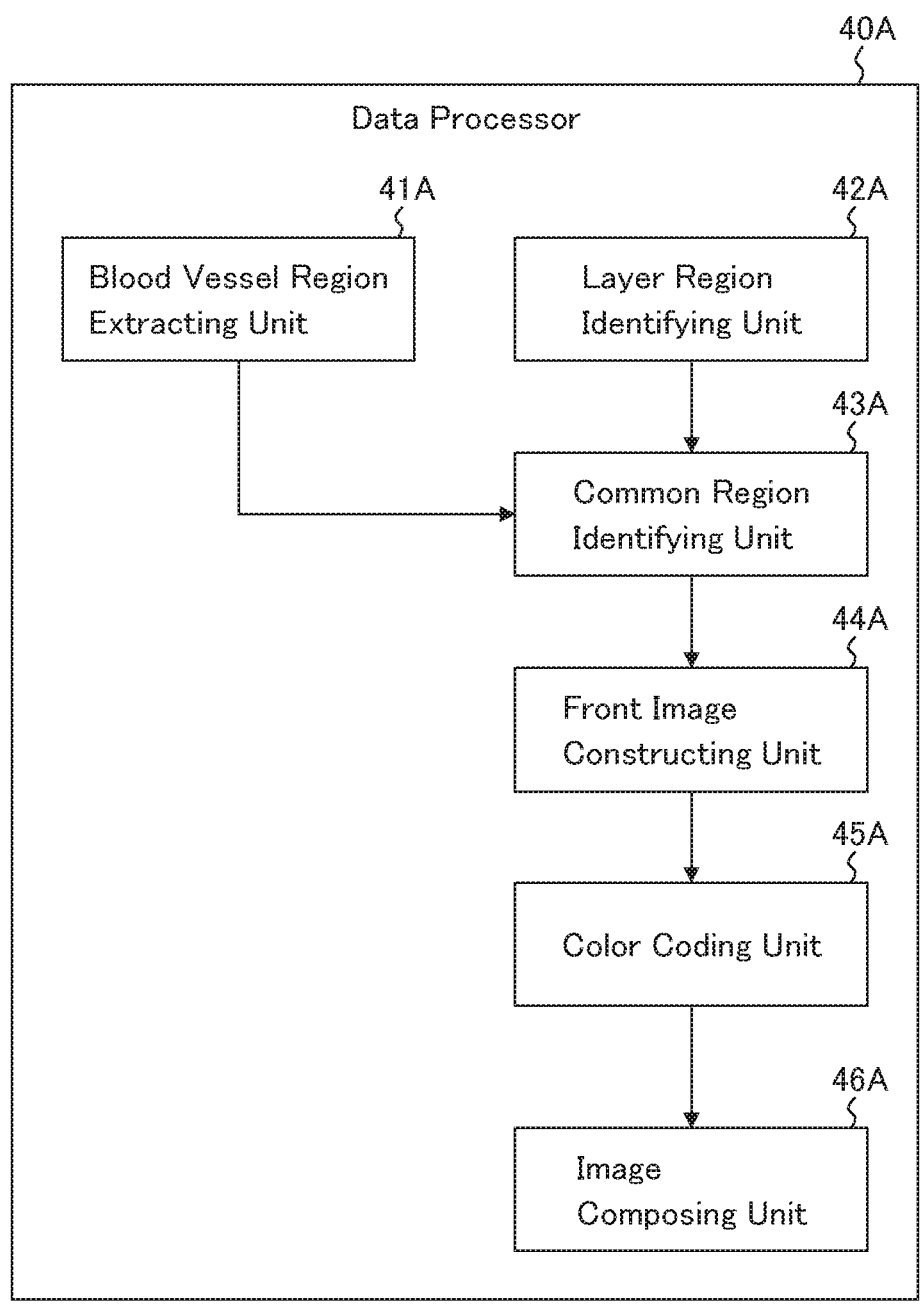
FIG. 2 is a schematic diagram illustrating an example of the configuration of the ophthalmological device according to the exemplary embodiment.

The data processor 40A shown in FIG. 2 is an example of the data processor 40. The data processor 40A of the present example includes the blood vessel region extracting unit 41A, the layer region identifying unit 42A, the common region identifying unit 43A, the front image constructing unit 44A, the color coding unit 45A, and the image composing unit 46A.

(Blood Vessel Region Extracting Unit 41A)

The blood vessel region extracting unit 41A is configured to extract a blood vessel region from a three dimensional data set of the subject's eye. The three dimensional data set is image data for displaying a blood vessel emphasized front image. The three dimensional data set may be the three dimensional data set 21 stored in the memory 20.

For example, in the event that the three dimensional data set 21 is a three dimensional data set that includes a plurality of B-scan images arranged in time series for each B cross section, the blood vessel region extracting unit 41A (or another element of the data processor 40A) performs the position matching (registration) of the B-scan images and the identification of the blood vessel regions in the manner described above. Furthermore, the blood vessel region extracting unit 41A (or another element of the data processor 40A) may assign, to the identified blood vessel regions, information indicating the fact that they are identified as blood vessels.

In another example, in the event that the three dimensional data set 21 is a three dimensional data set that includes a plurality of B-scan images arranged in time series for each B cross section, and in which the position matching (registration) of the B-scan images has already been performed, the blood vessel region extracting unit 41A (or another element of the data processor 40A) performs the identification of the blood vessel regions in the manner described above. Furthermore, the blood vessel region extracting unit 41A (or another element of the data processor 40A) may assign, to the identified blood vessel regions, information indicating the fact that they are identified as blood vessels.

In yet another example, the three dimensional data set 21 may be a three dimensional data set that includes a plurality of B-scan images arranged in time series for each B cross section, and in which the position matching (registration) of the B-scan images and the identification of the blood vessel regions both have already been performed. If this is the case, the blood vessel region extracting unit 41A (or another element of the data processor 40A) may assign, to the identified blood vessel regions, information indicating the fact that they are identified as blood vessels.

In the case where the information indicating the blood vessel regions is already given to the three dimensional data set 21, the blood vessel region extracting unit 41A may identify the blood vessel regions in the three dimensional data set 21 by referring to this information, and extract the identified blood vessel regions from the three dimensional data set 21.

On the other hand, in the case where the information indicating the blood vessel regions is not given to the three dimensional data set 21, the blood vessel region extracting unit 41A performs a process for identifying the blood vessel regions in the three dimensional data set 21. As described above, the blood vessel region identification may include a process of searching for image regions that change between the plurality of B-scan images to which the registration have been applied. Alternatively, the blood vessel region identification may include image processing such as edge detection or region growing. The blood vessel region extracting unit 41A extracts the identified blood vessel regions from the three dimensional data set 21.

The process of "extracting blood vessel regions from a three dimensional data set" may be, for example, a process of taking out the blood vessel regions from the three dimensional data set or a process of deleting image regions other than the blood vessel regions from the three dimensional data set. In an image frame that includes a blood vessel region extracted from the three dimensional data set, the pixel values in regions other than the blood vessel region are set to a default value (e.g., brightness value=0, R (red) value=G (green) value=B (blue) value=0, etc.). Such a default value is a pixel value corresponding to the background of the blood vessel region.

(Layer Region Identifying Unit 42A)

The layer region identifying unit 42A is configured to identify a plurality of layer regions by applying segmentation to the three dimensional data set of the subject's eye. Segmentation is generally a process of partitioning image data into a plurality of regions (segments). In the present example, segmentation is a process of identifying an image region corresponding to a specific tissue (a specific tissue boundary) of the subject's eye.

In a typical example, a three dimensional data set is acquired by applying a three dimensional OCT scan to an eye fundus and represents the layer structure of the eye fundus. Such a three dimensional data set represents the retina, choroid, sclera, vitreous body, and other tissues. More specifically, the following tissues are depicted in the three dimensional data set: inner limiting membrane, nerve fiber layer, ganglion cell layer, inner plexiform layer, inner nuclear layer, outer plexiform layer, outer nuclear layer, external limiting membrane, retinal pigment epithelium, Bruch's membrane, choroid, choroid-sclera interface, sclera, vitreous body, etc.

The layer region identifying unit 42A identifies a plurality of layer regions in such a three dimensional data set. The types of layer regions to be identified are set in advance. In addition or instead, the ophthalmological device 1 may be configured so that the user can set a desired type of a layer region. In addition or instead, the layer region identifying unit 42A may be configured to automatically set a type of layer regions to be identified by itself (Common Region Identifying Unit 43A)

For each of the plurality of layer regions identified by the layer region identifying unit 42A, the common region identifying unit 43A identifies a common region between that layer region and the blood vessel region extracted by the blood vessel region extracting unit 41A.

Typically, the three dimensional data set processed by the blood vessel region extracting unit 41A is substantially the same as the three dimensional data set processed by the layer region identifying unit 42A. That is, these three dimensional data sets are created from the same original data at least. Accordingly, there is no necessity to perform position matching (registration) between the layer region and the blood vessel region.

In the event that the three dimensional data set processed by the blood vessel region extracting unit 41A and the three dimensional data set processed by the layer region identifying unit 42A are substantially different from one another, registration (image matching) may be applied to these two three dimensional data sets.

For example, the common region identifying unit 43A is configured to, for example, compare the three dimensional coordinate values of the pixels included in the layer region with the three dimensional coordinate values of the pixels included in the blood vessel region, thereby identifying a set (pair) of a pixel in the layer region and a pixel in the blood vessel region whose three dimensional coordinate values are the same.

With this, a blood vessel region included in a layer region is identified for each of the plurality of layer regions identified by the layer region identifying unit 42A. In other words, the blood vessel regions (the three dimensional distribution of blood vessels) extracted by the blood vessel region extracting unit 41A is partitioned into a plurality of segments (partial regions) respectively corresponding to the plurality of layer regions identified by the layer region identifying unit 42A.

(Front Image Constructing Unit 44A)

The front image constructing unit 44A is configured to construct a front image based on each of the plurality of common regions identified by the common region identifying unit 43A. A common region may be, for example, a blood vessel region extracted by the blood vessel region extracting unit 41A. That is, a common region may be an image frame that includes a blood vessel region extracted by the blood vessel region extracting unit 41A. The image frame is typically a three dimensional image region corresponding to a specific layer (one or more layer tissues) of the eye fundus. The front image constructing unit 44A projects (integrates) the three dimensional image region in a predetermined direction (e.g., in the Z direction) to construct a shadowgram.

With this, a plurality of front images respectively corresponding to the plurality of layer regions identified by the layer region identifying unit 42A are obtained. Typically, a plurality of front images respectively corresponding to a plurality of different depth ranges in the eye fundus are obtained. Each front image depicts only part of the blood vessel regions extracted by the blood vessel region extracting unit 41A. That is, each front image depicts a corresponding common region.

(Color Coding Unit 45A)

The color coding unit 45A is configured to assign mutually different color information to the plurality of front images constructed by the front image constructing unit 44A.

For example, in the event that N number of front images $G_n$ (n=1, 2, . . . , N) are obtained by the front image constructing unit 44A, the color coding unit 45A assigns the first color to the first front image $G_1$, the second color to the second front image $G_2$, the N-th color to the N-th front image $G_N$. Here, the first color, the second color, . . . , the N-th color are different colors from each other. Note that the n-th color does not have to be of a single color tone and may include two or more color tones.

Further, the gradation of the n-th color is arbitrary. For example, the n-th color having a fixed gradation may be assigned to the n-th front image $G_n$. Alternatively, for each pixel of the n-th front image $G_n$ (or, for each pixel of the blood vessel regions included in the n-th front image $G_n$), an n-th color having a gradation value corresponding to the pixel value (brightness value) of a pixel may be assigned to this pixel. Here, the number of gradations of the pixel value may be the same as or different from the number of gradations of the n-th color. In the event that these number of gradations are different from one another, any known gradation conversion may be applied these gradations.

(Image Composing Unit 46A)

The image composing unit 46A composes at least two of the plurality of front images to which color information has been assigned by the color coding unit 45A. The front image obtained by this image composition is referred to as a composite front image. Various methods and techniques are known for composing two or more images.

In general image composition, registration is applied to two or more images to be composed. On the other hand, the present example is configured to construct a plurality of front images from a single three dimensional data set, and therefore does not require such registration.

A composite front image may be single image data. In the case where two or more front images are displayed in an overlapping manner using a layer display function or the like, the displayed images all in one piece may be treated as a composite front image.

In a typical example, a composite front image is an image of eye fundus blood vessels that has been color-coded according to layer regions. In other words, a composite front image is an image of blood vessels with colors associated with depth positions of eye fundus.

Figure 3:
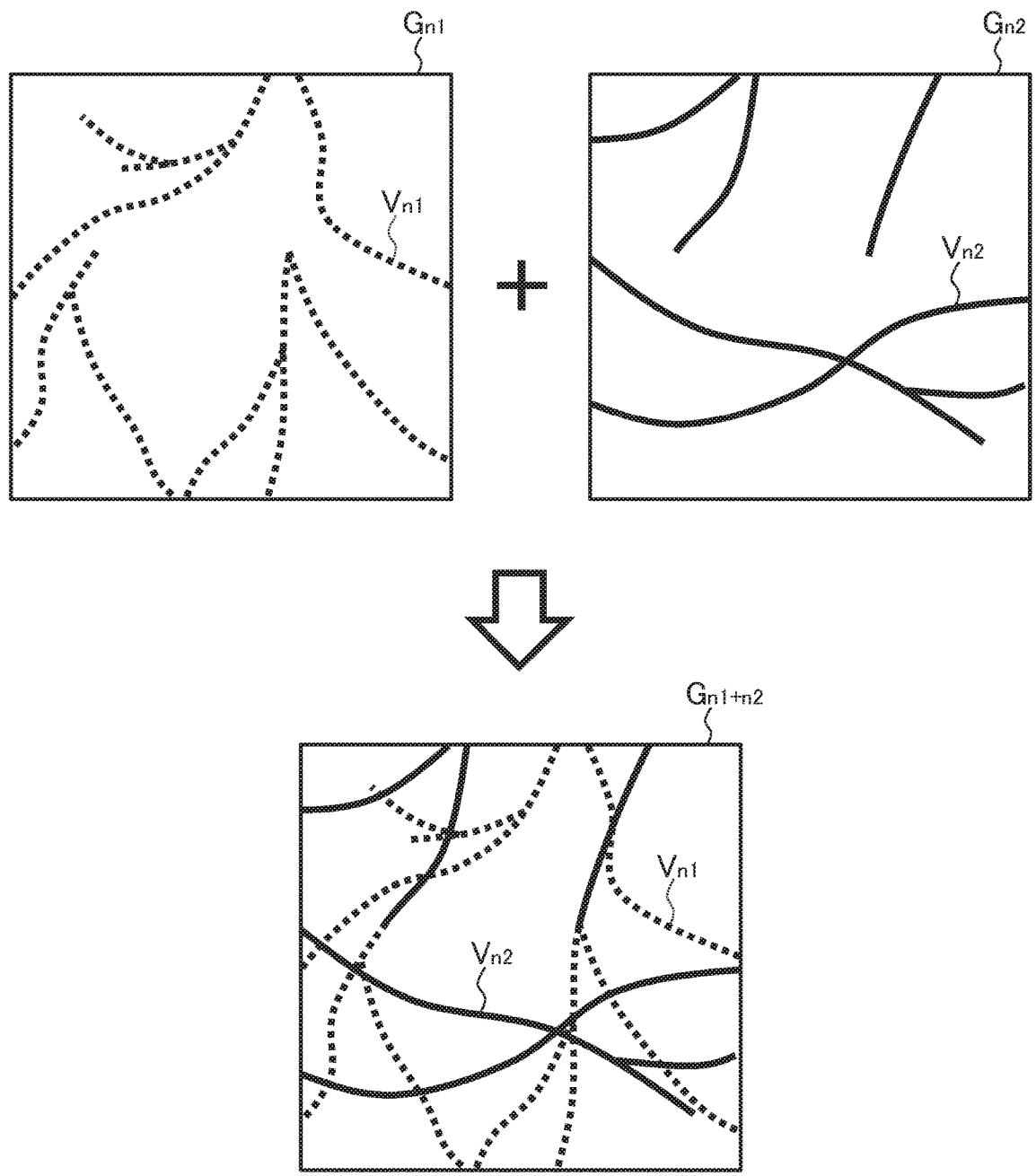
FIG. 3 is a schematic diagram illustrating an example of the image composition processing executed by the ophthalmological device according to the exemplary embodiment.

FIG. 3 shows an example of processing for constructing a composite front image. In the present example, the image composing unit 46A composes any two front images $G_{n1}$ and $G_{n2}$ out of the N number of front images $G_n$ (n=1, 2, . . . , N). Note that the number of front images to be composed is arbitrary, and the selection of front images to be composed is also arbitrary.

For description, the blood vessel region $V_{n1}$ in the front image $G_{n1}$ is indicated by a dotted line, and the blood vessel region $V_{n2}$ in the front image $G_{n2}$ is indicated by a solid line. The n1-th color is assigned to the blood vessel region $V_{n1}$ in the front image $G_{n1}$, and the n2-th color is assigned to the blood vessel region $V_{n2}$ in the front image $G_{n2}$.

The image composing unit 46A constructs the composite front image $G_{n1+n2}$ by composing the front images $G_{n1}$ and $G_{n2}$. In the composed front image $G_{n1+n2}$, the blood vessel region $V_{n1}$ in the n1-th color and the blood vessel region $V_{n2}$ in the n2-th color are depicted.

The display controller 11 may display the composite front image $G_{n1+n2}$ on the display unit 2. Instead of the image composing unit 46A constructing the composite front image $G_{n1+n2}$, the following display control may be performed. That is, the display controller 11 may set the first display layer and the second display layer to the display unit 2, and display the front images $G_{n1}$ and $G_{n2}$ respectively on the first and second display layers. The images displayed in this way also correspond to the composite front image $G_{n1+n2}$.

The display controller 11 may display various kinds of information together with the composite front image $G_{n1+n2}$. The incidental information (supplementary information) displayed together with the composite front image $G_{n1+n2}$ includes, for example, information indicating the positions (e.g., depth positions, depth ranges) of the blood vessel regions $V_{n1}$ and $V_{n2}$.

An example of such position information includes a color bar. The color bar is information representing the depth position of the blood vessel region $V_{n1}$ and the depth position of the blood vessel region $V_{n2}$ depicted in the composite front image $G_{n1+n2}$ as color information. In this case, the color information includes at least information on the n1-th color and information on the n2-th color.

Figure 4A:
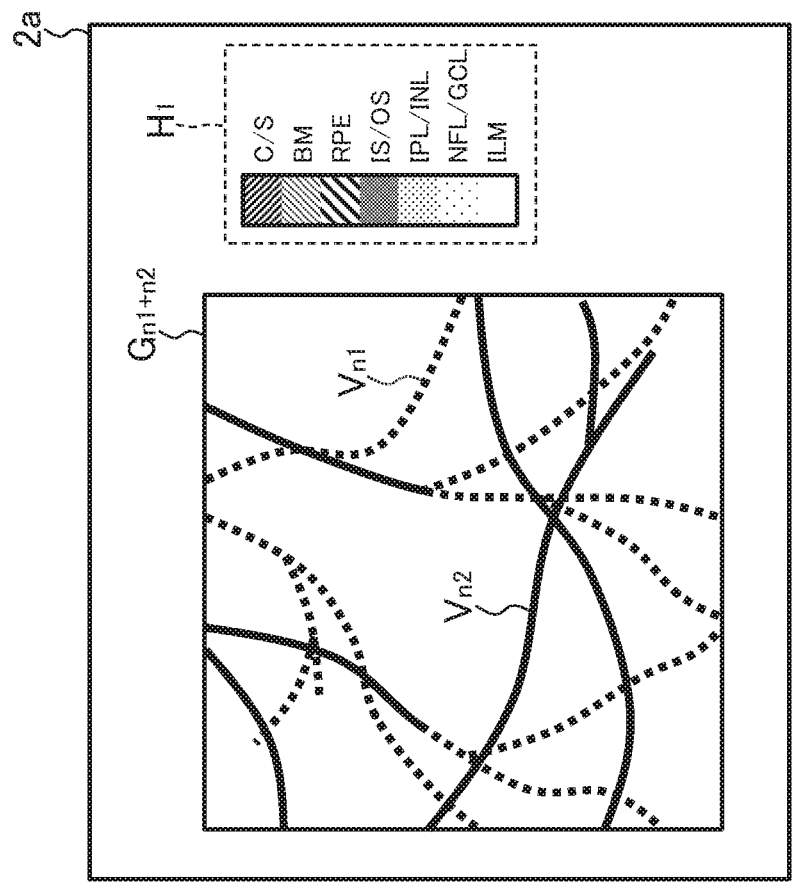
FIG. 4A is a schematic diagram illustrating an example of the display processing executed by the ophthalmological device according to the exemplary embodiment.
Figure 4B:
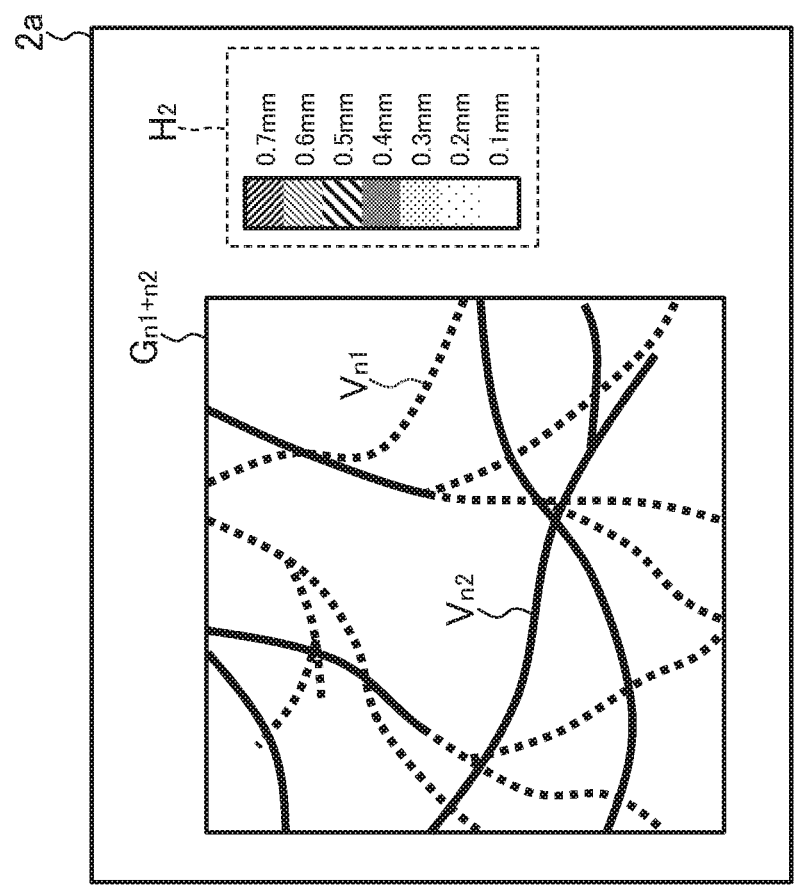
FIG. 4B is a schematic diagram illustrating an example of the display processing executed by the ophthalmological device according to the exemplary embodiment.

FIG. 4A and FIG. 4B shows two examples of color bars. In the example illustrated in FIG. 4A, the display controller 11 displays the composite front image $G_{n1+n2}$ and the color bar $H_1$ on the display screen 2a of the display unit 2. The color bar $H_1$ indicates the relationship between display colors and sites (tissues) of eye fundus. Here, "C/S" indicates the area from the choroid to the sclera, "BM" indicates the Bruch's membrane, "RPE" indicates the retinal pigment epithelium, "IS/OS" indicates the photoreceptor inner/outer segment junction (or the ellipsoid zone), "IPL/INL" indicates the area from the inner plexiform layer to the inner nuclear layer, "NFL/GCL" indicates the area from the nerve fiber layer and the ganglion cell layer, and "ILM" indicates the inner limiting membrane. These sites are identified by the above-mentioned segmentation, for example.

In the example shown in FIG. 4B, the display controller 11 displays the composite front image $G_{n1+n2}$ and the color bar $H_2$ on the display screen 2a of the display unit 2. The color bar $H_2$ indicates the relationship between display colors and depth positions (depth ranges). Here, the depth positions are defined by distances from the fundus surface (e.g., retinal surface, inner limiting membrane), for example. Further, a depth position (distance from the fundus surface) is calculated by, for example, any known eye fundus layer thickness analysis.

In the first embodiment, the memory 20 corresponds to the memory, the blood vessel region extracting unit 41A corresponds to the first blood vessel region extracting unit, the layer region identifying unit 42A corresponds to the first layer region identifying unit, and the common region identifying unit 43A corresponds to the first common region identifying unit, the front image constructing unit 44A corresponds to the first front image constructing unit, the color coding unit 45A corresponds to the first color coding unit, and the image composing unit 46A corresponds to the first image composing unit. In addition, the display unit 2 corresponds to the display device, and the display controller 11 corresponds to the display controller.

Second Embodiment

Figure 5:
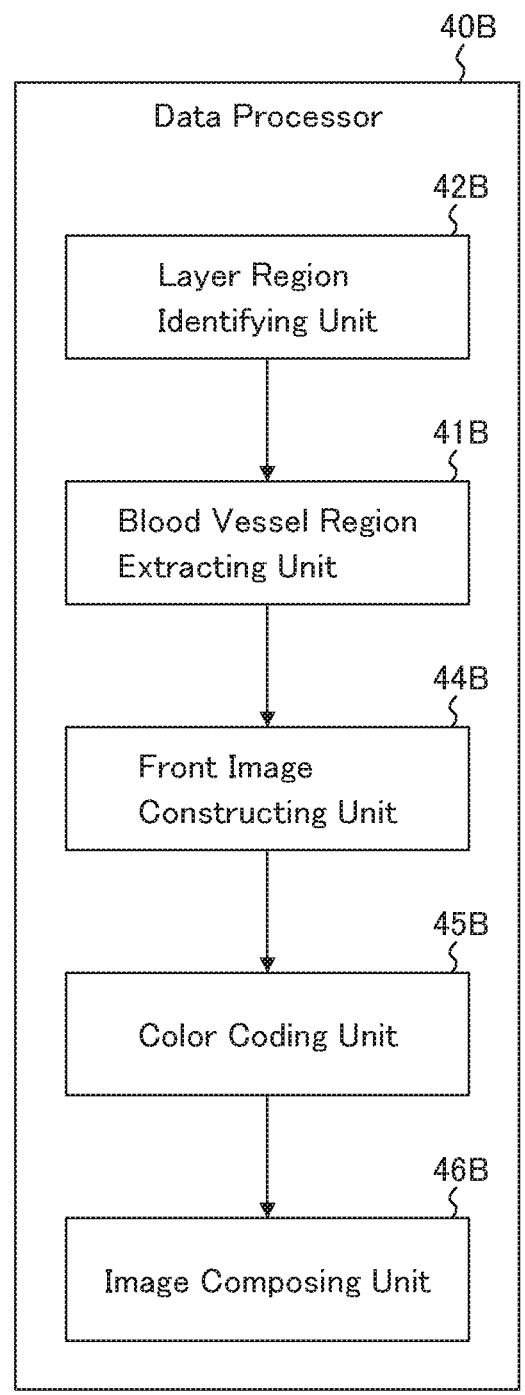
FIG. 5 is a schematic diagram illustrating an example of the configuration of the ophthalmological device according to the exemplary embodiment.

The ophthalmological device according to the second embodiment will be described. As in the first embodiment, the ophthalmological device according to the second embodiment includes the controller 10, the memory 20, the data input and output unit 30, the data processor 40, and the operation unit 50 (see FIG. 1). The difference between the second embodiment and the first embodiment is the configurations of the data processor 40. FIG. 5 shows an example of the data processor 40 in the second embodiment.

The data processor 40B shown in FIG. 5 includes the layer region identifying unit 42B, the blood vessel region extracting unit 41B, the front image constructing unit 44B, the color coding unit 45B, and the image composing unit 46B. Similar to the first embodiment, the three dimensional data set 21 obtained by applying OCT scanning to the subject's eye is stored in the memory 20.

The layer region identifying unit 42B is configured to identify a plurality of layer regions by applying segmentation to the three dimensional data set 21. This process is executed, for example, in the same manner as that executed by the layer region identifying unit 42A of the first embodiment.

The blood vessel region extracting unit 41B is configured to extract a blood vessel region from each of the plurality of layer regions identified by the layer region identifying unit 42B. This process is executed, for example, in the same manner as that executed by the blood vessel region extracting unit 41A of the first embodiment.

The front image constructing unit 44B is configured to construct a front image based on each of the plurality of blood vessel regions extracted by the blood vessel region extracting unit 41B. This process is executed, for example, in the same manner as that executed by the front image constructing unit 44A of the first embodiment.

The color coding unit 45B is configured to assign mutually different color information to the plurality of front images constructed by the front image constructing unit 44B. This process is executed, for example, in the same manner as that executed by the color coding unit 45A of the first embodiment.

The image composing unit 46B is configured to compose at least two of the plurality of front images to which the color information has been assigned by the color coding unit 45B, to construct a composite front image. This process is executed, for example, in the same manner as that executed by the image composing unit 46A of the first embodiment.

According to the ophthalmological device of the second embodiment configured as described above, a composite front image such as the composite front image $G_{n1+n2}$ illustrated in FIG. 3 can be constructed. Furthermore, the ophthalmological device of the second embodiment is capable of displaying a composite front image and any incidental information as exemplified in FIG. 4A and FIG. 4B.

In the second embodiment, the memory 20 corresponds to the memory, the layer region identifying unit 42B corresponds to the second layer region identifying unit, the blood vessel region extracting unit 41B corresponds to the second blood vessel region extracting unit, the front image constructing unit 44B corresponds to the second front image constructing unit, the color coding unit 45B corresponds to the second color coding unit, and the image composing unit 46B corresponds to the second image composing unit. In addition, the display unit 2 corresponds to the display device, and the display controller 11 corresponds to the display controller.

Third Embodiment

Figure 6:
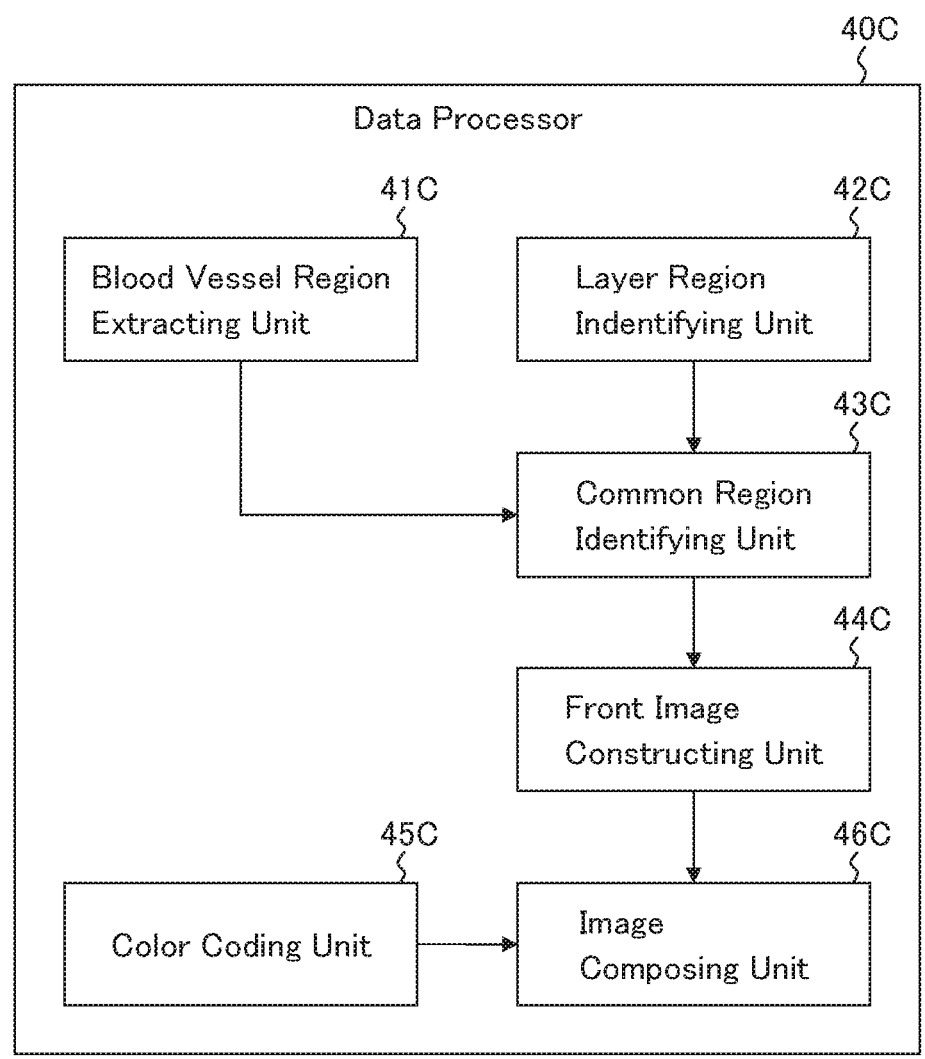
FIG. 6 is a schematic diagram illustrating an example of the configuration of the ophthalmological device according to the exemplary embodiment.

The ophthalmological device according to the third embodiment will be described. As in the first embodiment, the ophthalmological device according to the third embodiment includes the controller 10, the memory 20, the data input and output unit 30, the data processor 40, and the operation unit 50 (see FIG. 1). The difference between the third embodiment and the first embodiment is the configurations of the data processor 40. FIG. 6 shows an example of the data processor 40 in the third embodiment.

The data processor 40C shown in FIG. 6 includes the color coding unit 45C, the blood vessel region extracting unit 41C, the layer region identifying unit 42C, the common region identifying unit 43C, the front image constructing unit 44C, and the image composing unit 46C. Similar to the first embodiment, the three dimensional data set 21 obtained by applying OCT scanning to the subject's eye is stored in the memory 20.

The color coding unit 45C is configured to assign color information corresponding to (according to) depth positions to the three dimensional data set 21.

For example, the color coding unit 45C is configured to partition the range in the depth direction in which the three dimensional data set 21 is defined into a plurality of sections, and assign mutually different colors to the sections partitioned. Here, the range in the depth direction in which the three dimensional data set 21 is defined is the domain of definition of the three dimensional data set 21 in the Z direction.

In another example, the color coding unit 45C is configured to assign substantially continuously changing color information to the domain of definition of the three dimensional data set 21 in the Z direction. Here, the substantially continuously changing color information may be color information in which gradations change continuously.

The method of assigning color information to the three dimensional data set 21 is not limited to the above examples. In general, the specific processing content for color information association may be optional, as long as it allows the user to recognize the position and/or the range (area) in the Z direction based on color vision.

The blood vessel region extracting unit 41C is configured to extract a blood vessel region from the three dimensional data set 21. This process is executed, for example, in the same manner as that executed by the blood vessel region extracting unit in any of the embodiments described above.

The layer region identifying unit 42C is configured to identify a plurality of layer regions by applying segmentation to the three dimensional data set 21. This process is executed, for example, in the same manner as that executed by the layer region identifying unit in any of the embodiments described above.

The common region identifying unit 43C is configured to identify a common region between the layer region and the blood vessel region identified by the blood vessel region extracting unit 41C, for each of the plurality of layer regions identified by the layer region identifying unit 42C. This process is executed, for example, in the same manner as that executed by the common region identifying unit in any of the embodiments described above.

The front image constructing unit 44C is configured to construct a front image based on each of the plurality of common regions identified by the common region identifying unit 43C. This process is executed, for example, in the same manner as that executed by the front image constructing unit in any of the embodiments described above.

The image composing unit 46C is configured to compose at least two of the plurality of front images constructed by the front image constructing unit 44C based on the color information assigned to the three dimensional data set 21 by the color coding unit 45C, thereby constructing a composite front image.

For example, the image composing unit 46C is configured to identify color information corresponding to a front image, for each of two or more front images supplied for the image composition processing. As a specific example thereof, the image composing unit 46C is configured to, for each of two or more front images supplied for the image composition processing, identify the depth range of the layer region corresponding to a front image (i.e., the depth range in the three dimensional data set 21), and identify the color information assigned to the depth range identified. Here, in the event that there are two or more pieces of color information assigned to the identified depth range, any one of these pieces of color information may be selected as representative color information.

For example, in the case where stepwise color information is assigned to the three dimensional data set 21, and in the event that two or more pieces of color information have been assigned to the identified depth range, the image composing unit 46C may select the color information on the deepest side, the color information on the shallowest side, or the color information located at the center. Alternatively, the image composing unit 46C may select the color information, among the two or more pieces of color information, that is assigned to the widest range within the identified depth range.

In addition or instead, part or all of the plurality of pieces of color information assigned to the identified depth range may be used.

In the event that continuous color information is assigned to the three dimensional data set 21, the image composing unit 46C may select any of the color information corresponding to the identified depth range. For example, the image composing unit 46C may select the color information on the deepest side, the color information on the shallowest side, or the color information located at the center. In addition or instead, part or all of the continuous color information may be used.

The image composing unit 46C constructs a composite front image by composing two or more front images based on color information as described above. The composition of front images is executed, for example, in the same manner as that executed by the image composing unit in any of the embodiments described above.

According to the ophthalmological device of the third embodiment configured as described above, a composite front image such as the composite front image $G_{n1+n2}$ illustrated in FIG. 3 can be constructed. Furthermore, the ophthalmological device is capable of displaying a composite front image and incidental information, as illustrated in FIG. 4A and FIG. 4B.

In the third embodiment, the memory 20 corresponds to the memory, the color coding unit 45C corresponds to the third color coding unit, the blood vessel region extracting unit 41C corresponds to the third blood vessel region extracting unit, the layer region identifying unit 42C corresponds to the third layer region identifying unit, the common region identifying unit 43C corresponds to the third common region identifying unit, the front image constructing unit 44C corresponds to the third front image constructing unit, and the image composing unit 46C corresponds to the third image composing unit. In addition, the display unit 2 corresponds to the display device, and the display controller 11 corresponds to the display controller.

Fourth Embodiment

Figure 7:
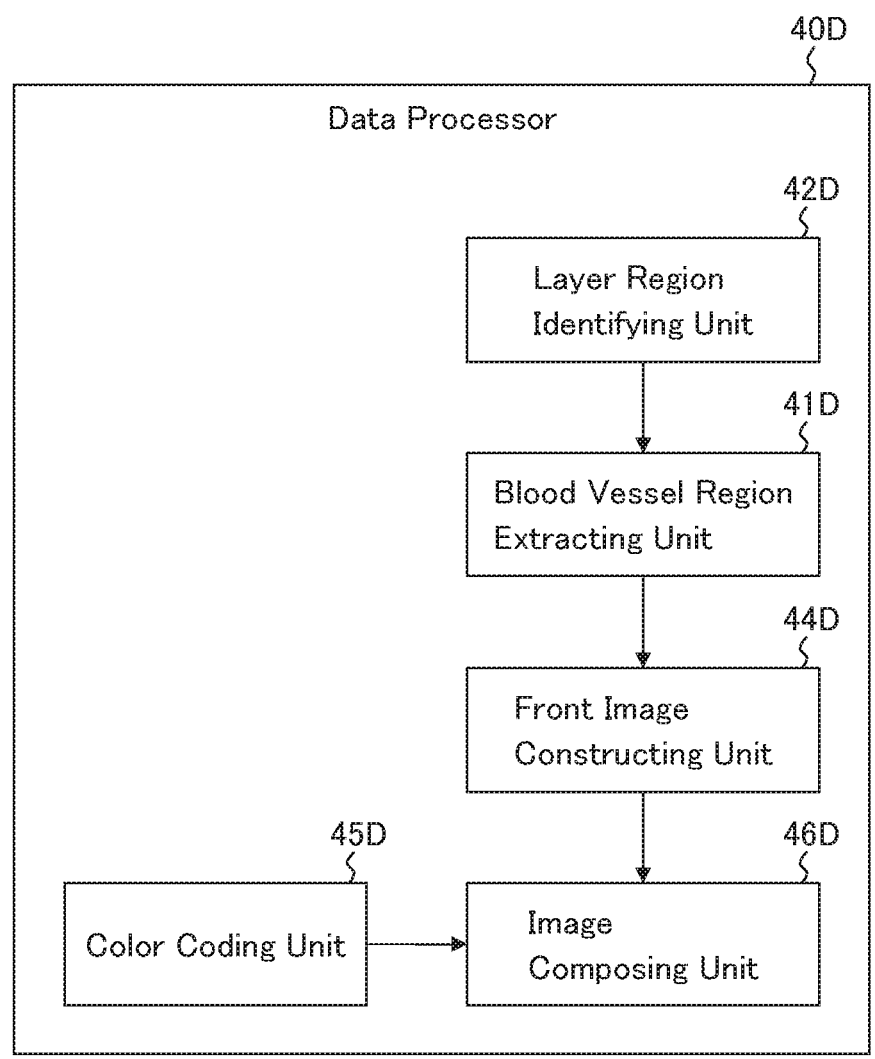
FIG. 7 is a schematic diagram illustrating an example of the configuration of the ophthalmological device according to the exemplary embodiment.

The ophthalmological device according to the fourth embodiment will be described. As in the first embodiment, the ophthalmological device according to the fourth embodiment includes the controller 10, the memory 20, the data input and output unit 30, the data processor 40, and the operation unit 50 (see FIG. 1). The difference between the fourth embodiment and the first embodiment is the configurations of the data processor 40. FIG. 7 shows an example of the data processor 40 in the fourth embodiment.

The data processor 40D shown in FIG. 7 includes the color coding unit 45D, the layer region identifying unit 42D, the blood vessel region extracting unit 41D, the front image constructing unit 44D, and the image composing unit 46D. Similar to the first embodiment, the three dimensional data set 21 obtained by applying OCT scanning to the subject's eye is stored in the memory 20.

The color coding unit 45D is configured to assign color information corresponding to depth positions, to the three dimensional data set 21. This process is executed, for example, in the same manner as that executed by the color coding unit of any of the embodiments described above.

The layer region identifying unit 42D is configured to identify a plurality of layer regions by applying segmentation to the three dimensional data set 21. This process is executed, for example, in the same manner as that executed by the layer region identifying unit in any of the embodiments described above.

The blood vessel region extracting unit 41D is configured to extract a blood vessel region from each of the plurality of layer regions identified by the layer region identifying unit 42D. This process is executed, for example, in the same manner as that executed by the blood vessel region extracting unit of any of the embodiments described above.

The front image constructing unit 44D is configured to construct a front image based on each of the plurality of blood vessel regions extracted by the blood vessel region extracting unit 41D. This process is executed, for example, in the same manner as that executed by the front image constructing unit in any of the embodiments described above.

The image composing unit 46D is configured to construct a composite front image by composing at least two of the plurality of front images constructed by the front image constructing unit 44D based on the color information assigned to the three dimensional data set 21 by the color coding unit 45D. This process is executed, for example, in the same manner as that executed by the image composing unit in any of the embodiments described above.

According to the ophthalmological device of the fourth embodiment configured as described above, a composite front image such as the composite front image $G_{n1+n2}$ illustrated in FIG. 3 can be constructed. Furthermore, the ophthalmological device is capable of displaying a composite front image and incidental information, as illustrated in FIG. 4A and FIG. 4B.

In the fourth embodiment, the memory 20 corresponds to the memory, the color coding unit 45D corresponds to the fourth color coding unit, the layer region identifying unit 42D corresponds to the fourth layer region identifying unit, the blood vessel region extracting unit 41D corresponds to the fourth blood vessel region extracting unit, the front image constructing unit 44D corresponds to the fourth front image constructing unit, and the image composing unit 46D corresponds to the fourth image composing unit. In addition, the display unit 2 corresponds to the display device, and the display controller 11 corresponds to the display controller.

Fifth Embodiment

Figure 8:
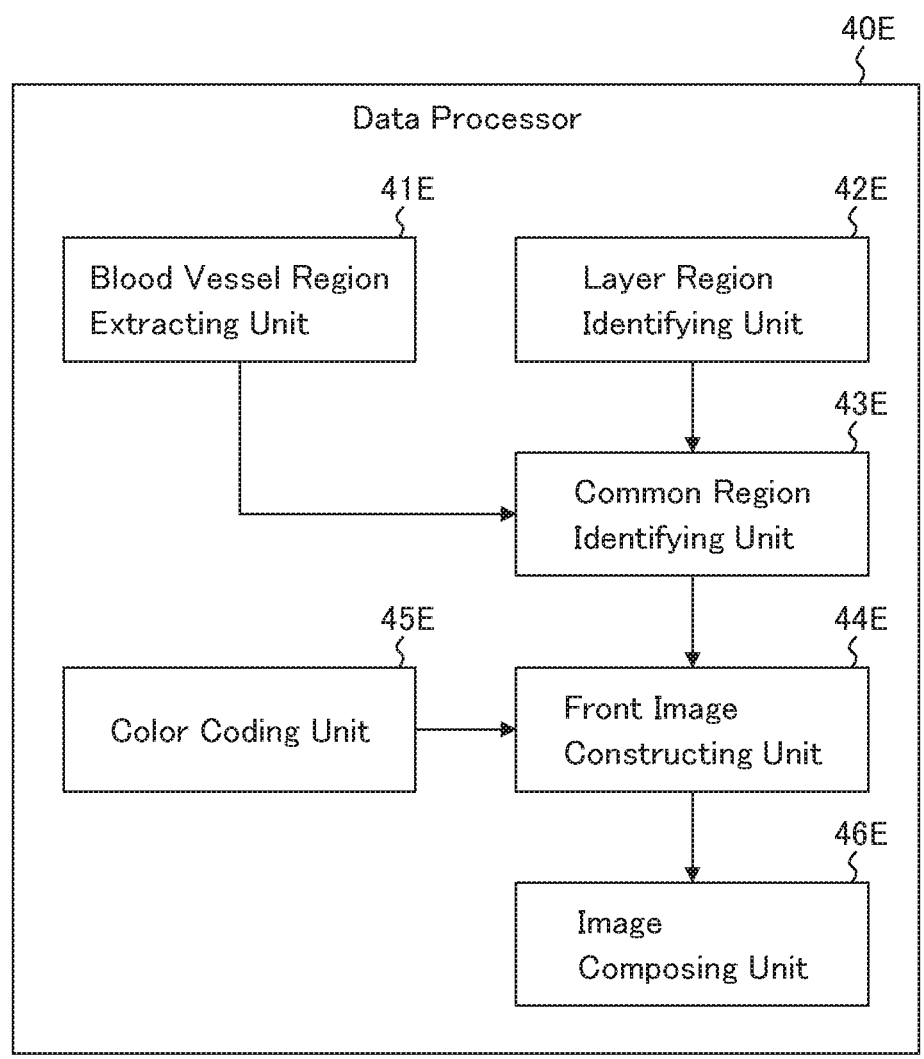
FIG. 8 is a schematic diagram illustrating an example of the configuration of the ophthalmological device according to the exemplary embodiment.

The ophthalmological device according to the fifth embodiment will be described. As in the first embodiment, the ophthalmological device according to the fourth embodiment includes the controller 10, the memory 20, the data input and output unit 30, the data processor 40, and the operation unit 50 (see FIG. 1). The difference between the fifth embodiment and the first embodiment is the configurations of the data processor 40. FIG. 8 shows an example of the data processor 40 in the fifth embodiment.

The data processor 40E shown in FIG. 8 includes the color coding unit 45E, the blood vessel region extracting unit 41E, the layer region identifying unit 42E, the common region identifying unit 43E, the front image constructing unit 44E, and the image composing unit 46E. Similar to the first embodiment, the three dimensional data set 21 obtained by applying OCT scanning to the subject's eye is stored in the memory 20.

The color coding unit 45E is configured to assign color information corresponding to depth positions, to the three dimensional data set 21. This process is executed, for example, in the same manner as that executed by the color coding unit of any of the embodiments described above.

The blood vessel region extracting unit 41E is configured to extract a blood vessel region from the three dimensional data set 21. This process is executed, for example, in the same manner as that executed by the blood vessel region extracting unit of any of the embodiments described above.

The layer region identifying unit 42E is configured to identify a plurality of layer regions by applying segmentation to the three dimensional data set 21. This process is executed, for example, in the same manner as that executed by the layer region identifying unit in any of the embodiments described above.

The common region identifying unit 43E is configured to identify a common region between a layer region and the blood vessel region identified by the blood vessel region extracting unit 41C, for each of the plurality of layer regions identified by the layer region identifying unit 42E. This process is executed, for example, in the same manner as that executed by the common region identifying unit in any of the embodiments described above.

The front image constructing unit 44E is configured to construct a front image, based on each of the plurality of common regions identified by the common region identifying unit 43E, and on the color information assigned to the three dimensional data set 21 by the color coding unit 45E.

For example, the front image constructing unit 44E is configured to identify the color information corresponding to a common region, for each of the plurality of common regions corresponding to the plurality of layer regions. As a specific example, the front image constructing unit 44E is configured to, for each of the plurality of common regions corresponding to the plurality of layer regions, identify the depth range of the layer region corresponding to a common region (i.e., the depth range in the three dimensional data set 21), and identify the color information assigned to the depth range identified. Here, in the event that a plurality of pieces of color information is assigned to the identified depth range, any one of these pieces of color information may be selected as representative color information. The front image constructing unit 44E may be configured to use part or all of the plurality of pieces of color information assigned to the identified depth range.

The front image constructing unit 44E may construct a front image based on such color information and a common region. For example, the front image constructing unit 44E may give color information to a common region, and construct a front image from the common region to which the color information has been given. Alternatively, the front image constructing unit 44E may construct a front image from a common region, and give color information to the constructed front image. Here, the process of constructing a front image from a common region is executed, for example, in the same manner as that executed by the front image constructing unit of any of the embodiments described above.

The image composing unit 46E is configured to compose at least two of the plurality of front images constructed by the front image constructing unit 44E, to construct a composite front image. This process is executed, for example, in the same manner as that executed by the image composing unit in any of the embodiments described above.

According to the ophthalmological device of the fifth embodiment configured as described above, a composite front image such as the composite front image $G_{n1+n2}$ illustrated in FIG. 3 can be constructed. Furthermore, the ophthalmological device si capable of displaying a composite front image and incidental information, as illustrated in FIG. 4A and FIG. 4B.

In the fifth embodiment, the memory 20 corresponds to the memory, the color coding unit 45E corresponds to the fifth color coding unit, the blood vessel region extracting unit 41E corresponds to the fifth blood vessel region extracting unit, the layer region identifying unit 42E corresponds to the fifth layer region identifying unit, the common region identifying unit 43E corresponds to the fifth common region identifying unit, the front image constructing unit 44E corresponds to the fifth front image constructing unit, and the image composing unit 46E corresponds to the fifth image composing unit. In addition, the display unit 2 corresponds to the display device, and the display controller 11 corresponds to the display controller.

Sixth Embodiment

Figure 9:
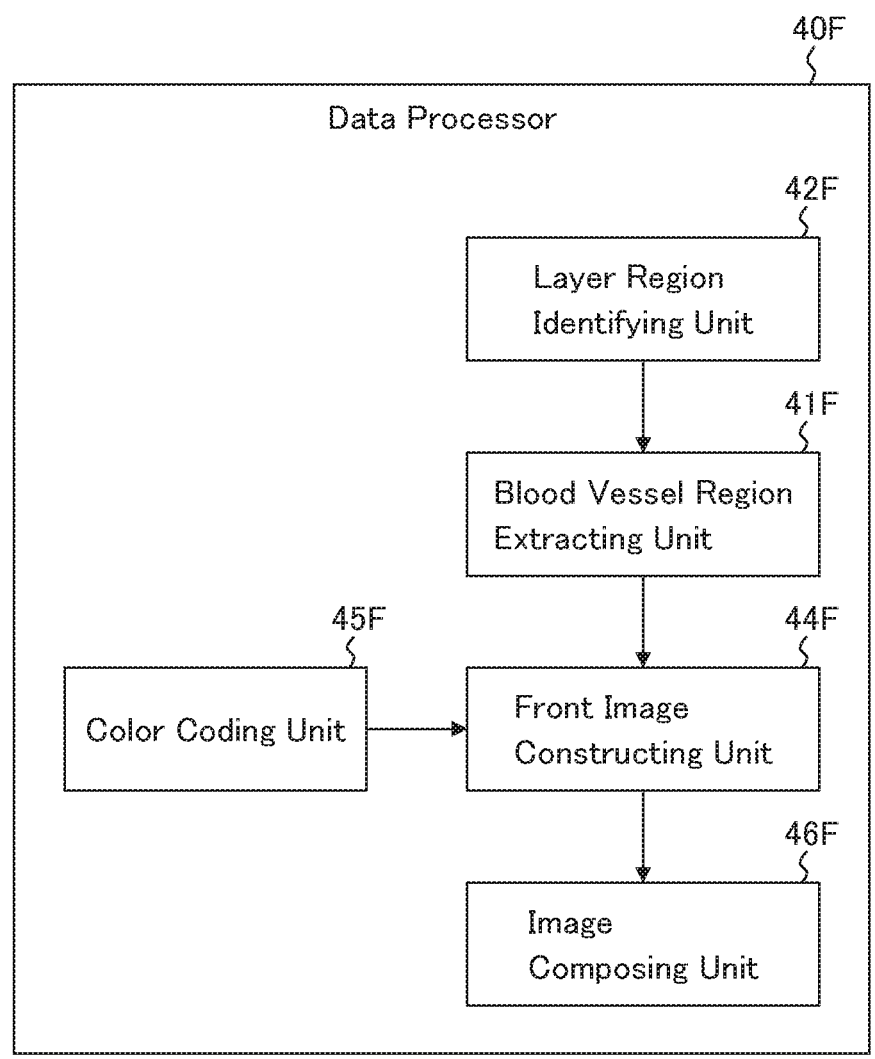
FIG. 9 is a schematic diagram illustrating an example of the configuration of the ophthalmological device according to the exemplary embodiment.

The ophthalmological device according to the sixth embodiment will be described. As in the first embodiment, the ophthalmological device according to the sixth embodiment includes the controller 10, the memory 20, the data input and output unit 30, the data processor 40, and the operation unit 50 (see FIG. 1). The difference between the sixth embodiment and the first embodiment is the configurations of the data processor 40. FIG. 9 shows an example of the data processor 40 in the sixth embodiment.

The data processor 40F shown in FIG. 9 includes the color coding unit 45F, the layer region identifying unit 42F, the blood vessel region extracting unit 41F, the front image constructing unit 44F, and the image composing unit 46F. Similar to the first embodiment, the three dimensional data set 21 obtained by applying OCT scanning to the subject's eye is stored in the memory 20.

The color coding unit 45F is configured to assign color information corresponding to depth positions, to the three dimensional data set 21. This process is executed, for example, in the same manner as that executed by the color coding unit of any of the embodiments described above.

The layer region identifying unit 42F is configured to identify a plurality of layer regions by applying segmentation to the three dimensional data set 21. This process is executed, for example, in the same manner as that executed by the layer region identifying unit in any of the embodiments described above.

The blood vessel region extracting unit 41F is configured to extract a blood vessel region from each of the plurality of layer regions identified by the layer region identifying unit 42F. This process is executed, for example, in the same manner as that executed by the blood vessel region extracting unit of any of the embodiments described above.

The front image constructing unit 44F is configured to construct a front image, based on each of the plurality of blood vessel regions extracted by the blood vessel region extracting unit 41F, and on the color information assigned to the three dimensional data set 21 by the color coding unit 45F. This process is executed, for example, in the same manner as that executed by the front image constructing unit in any of the embodiments described above.

The image composing unit 46F is configured to compose at least two of the plurality of front images constructed by the front image constructing unit 44F, to construct a composite front image. This process is executed, for example, in the same manner as that executed by the image composing unit in any of the embodiments described above.

According to the ophthalmological device of the sixth embodiment configured as described above, a composite front image such as the composite front image $G_{n1+n2}$ illustrated in FIG. 3 can be constructed. Furthermore, the ophthalmological device is capable of displaying a composite front image and incidental information, as illustrated in FIG. 4A and FIG. 4B.

In the sixth embodiment, the memory 20 corresponds to the memory, the color coding unit 45F corresponds to the sixth color coding unit, the layer region identifying unit 42F corresponds to the sixth layer region identifying unit, the blood vessel region extracting unit 41F corresponds to the sixth blood vessel region extracting unit, the front image constructing unit 44F corresponds to the sixth front image constructing unit, and the image composing unit 46F corresponds to the sixth image composing unit. In addition, the display unit 2 corresponds to the display device, and the display controller 11 corresponds to the display controller.

Seventh Embodiment

Figure 10:
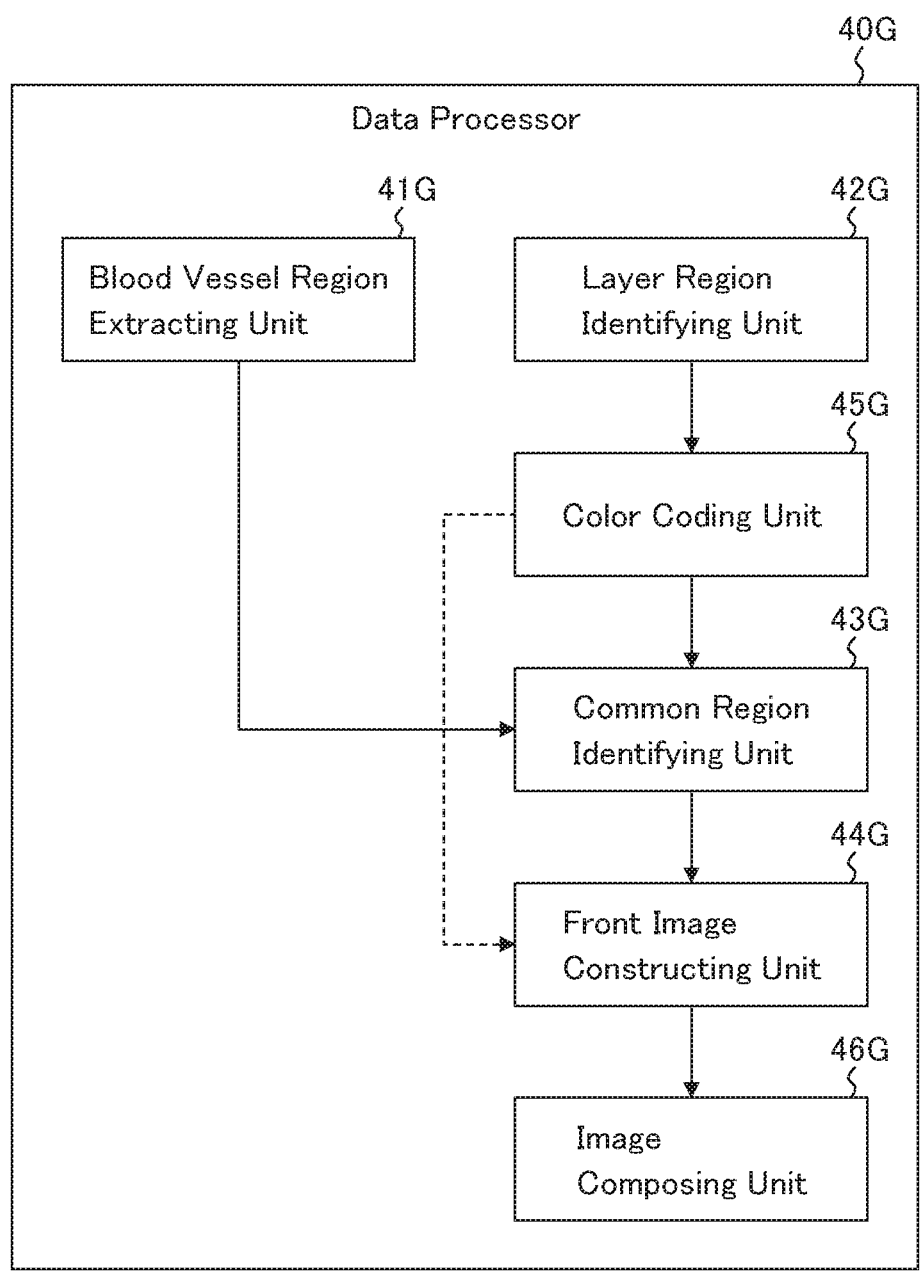
FIG. 10 is a schematic diagram illustrating an example of the configuration of the ophthalmological device according to the exemplary embodiment.

The ophthalmological device according to the seventh embodiment will be described. As in the first embodiment, the ophthalmological device according to the seventh embodiment includes the controller 10, the memory 20, the data input and output unit 30, the data processor 40, and the operation unit 50 (see FIG. 1). The difference between the seventh embodiment and the first embodiment is the configurations of the data processor 40. FIG. 10 shows an example of the data processor 40 in the seventh embodiment.

The data processor 40G shown in FIG. 10 includes the blood vessel region extracting unit 41G, the layer region identifying unit 42G, the color coding unit 45G, the common region identifying unit 43G, the front image constructing unit 44G, and the image composing unit 46G. Similar to the first embodiment, the three dimensional data set 21 obtained by applying OCT scanning to the subject's eye is stored in the memory 20.

The blood vessel region extracting unit 41G is configured to extract a blood vessel region from the three dimensional data set 21. This process is executed, for example, in the same manner as that executed by the blood vessel region extracting unit of any of the embodiments described above.

The layer region identifying unit 42G is configured to identify a plurality of layer regions by applying segmentation to the three dimensional data set 21. This process is executed, for example, in the same manner as that executed by the layer region identifying unit in any of the embodiments described above.

The color coding unit 45G is configured to assign mutually different color information to the plurality of layer regions identified by the layer region identifying unit 42G. This process is executed, for example, in the same manner as that executed by the color coding unit of any of the embodiments described above.

The common region identifying unit 43G is configured to, for each of the plurality of layer regions identified by the layer region identifying unit 42G, identify a common region between a layer region and the blood vessel region identified by the blood vessel region extracting unit 41G. This process is executed, for example, in the same manner as that executed by the common region identifying unit in any of the embodiments described above.

The front image constructing unit 44G is configured to construct a front image, based on each of the plurality of common regions identified by the common region identifying unit 43G, and on the color information assigned to the plurality of layer regions by the color coding unit 45G. This process is executed, for example, in the same manner as that executed by the front image constructing unit in any of the embodiments described above.

The image composing unit 46G is configured to compose at least two of the plurality of front images constructed by the front image constructing unit 44G, to construct a composite front image. This process is executed, for example, in the same manner as that executed by the image composing unit in any of the embodiments described above.

According to the ophthalmological device of the seventh embodiment configured as described above, a composite front image such as the composite front image $G_{n1+n2}$ illustrated in FIG. 3 can be constructed. Furthermore, the ophthalmological device is capable of displaying a composite front image and incidental information, as illustrated in FIG. 4A and FIG. 4B.

In the seventh embodiment, the memory 20 corresponds to the memory, the blood vessel region extracting unit 41G corresponds to the seventh blood vessel region extracting unit, the layer region identifying unit 42G corresponds to the seventh layer region identifying unit, the color coding unit 45G corresponds to the seventh color coding unit, the common region identifying unit 43G corresponds to the seventh common region identifying unit, the front image constructing unit 44G corresponds to the seventh front image constructing unit, and the image composing unit 46G corresponds to the seventh image composing unit. In addition, the display unit 2 corresponds to the display device, and the display controller 11 corresponds to the display controller.

Eighth Embodiment

Figure 11:
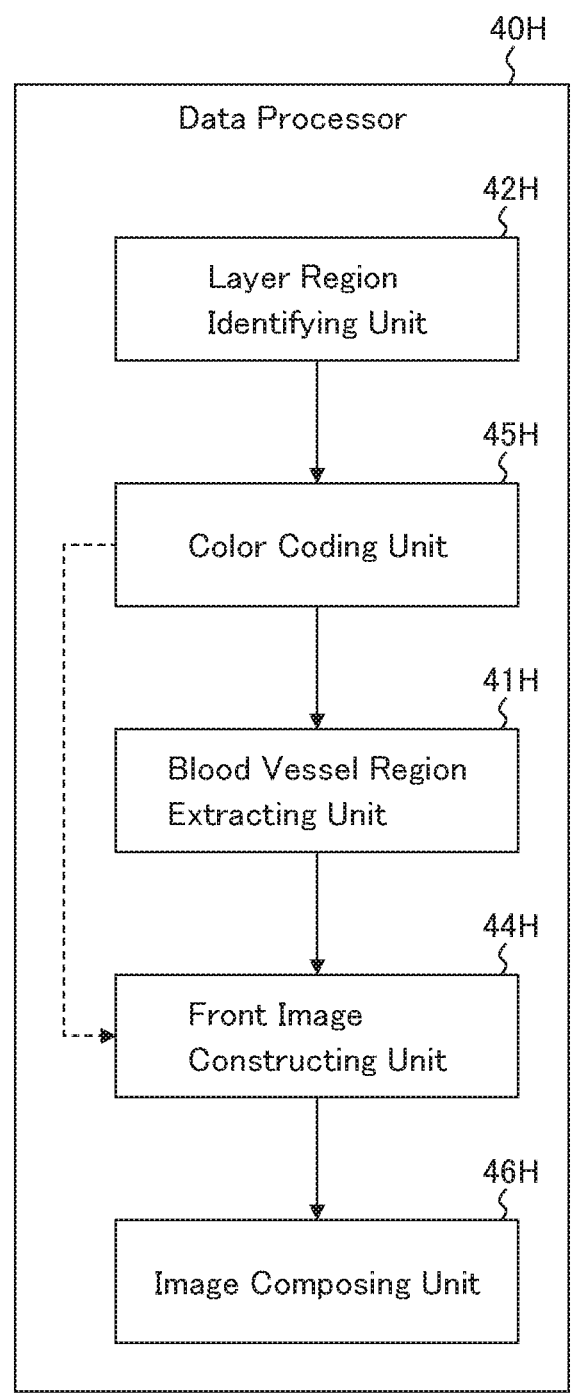
FIG. 11 is a schematic diagram illustrating an example of the configuration of the ophthalmological device according to the exemplary embodiment.

The ophthalmological device according to the eighth embodiment will be described. As in the first embodiment, the ophthalmological device according to the eighth embodiment includes the controller 10, the memory 20, the data input and output unit 30, the data processor 40, and the operation unit 50 (see FIG. 1). The difference between the eighth embodiment and the first embodiment is the configurations of the data processor 40. FIG. 11 shows an example of the data processor 40 in the eighth embodiment.

The data processor 40H shown in FIG. 11 includes the layer region identifying unit 42H, the color coding unit 45H, the blood vessel region extracting unit 41H, the front image constructing unit 44H, and the image composing unit 46H. Similar to the first embodiment, the three dimensional data set 21 obtained by applying OCT scanning to the subject's eye is stored in the memory 20.

The layer region identifying unit 42H is configured to identify a plurality of layer regions by applying segmentation to the three dimensional data set 21. This process is executed, for example, in the same manner as that executed by the layer region identifying unit in any of the embodiments described above.

The color coding unit 45H is configured to assign mutually different color information to the plurality of layer regions identified by the layer region identifying unit 42H. This process is executed, for example, in the same manner as that executed by the color coding unit of any of the embodiments described above.

The blood vessel region extracting unit 41H is configured to extract a blood vessel region from each of the plurality of layer regions identified by the layer region identifying unit 42H. This process is executed, for example, in the same manner as that executed by the blood vessel region extracting unit of any of the embodiments described above.

The front image constructing unit 44H is configured to construct a front image, based on each of the plurality of blood vessel regions extracted by the blood vessel region extracting unit 41H, and on the color information assigned to the plurality of layer regions by the color coding unit 45H. This process is executed, for example, in the same manner as that executed by the front image constructing unit in any of the embodiments described above.

The image composing unit 46H is configured to compose at least two of the plurality of front images constructed by the front image constructing unit 44H, to construct a composite front image. This process is executed, for example, in the same manner as that executed by the image composing unit in any of the embodiments described above.

According to the ophthalmological device of the eighth embodiment configured as described above, a composite front image such as the composite front image $G_{n1+n2}$ illustrated in FIG. 3 can be constructed. Furthermore, the ophthalmological device is capable of displaying a composite front image and incidental information, as illustrated in FIG. 4A and FIG. 4B.

In the eighth embodiment, the memory 20 corresponds to the memory, the layer region identifying unit 42H corresponds to the eighth layer region identifying unit, the color coding unit 45H corresponds to the eighth color coding unit, the blood vessel region extracting unit 41H corresponds to the eighth blood vessel region extracting unit, the front image constructing unit 44H corresponds to the eighth front image constructing unit, and the image composing unit 46H corresponds to the eighth image composing unit. In addition, the display unit 2 corresponds to the display device, and the display controller 11 corresponds to the display controller.

Ninth Embodiment

Figure 12:
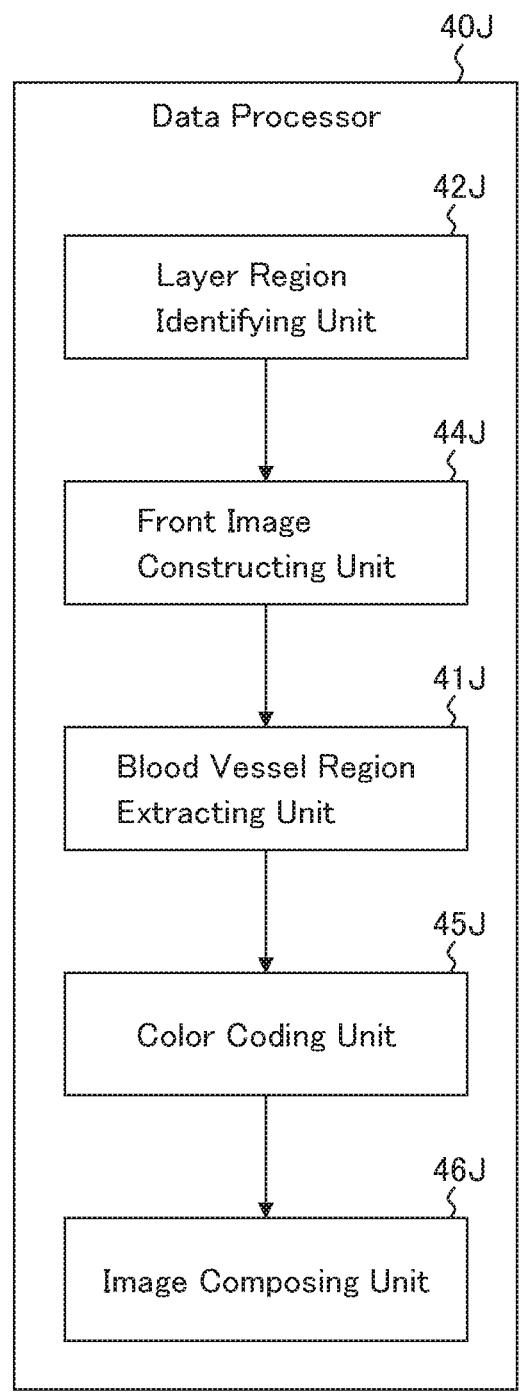
FIG. 12 is a schematic diagram illustrating an example of the configuration of the ophthalmological device according to the exemplary embodiment.

The ophthalmological device according to the ninth embodiment will be described. As in the first embodiment, the ophthalmological device according to the ninth embodiment includes the controller 10, the memory 20, the data input and output unit 30, the data processor 40, and the operation unit 50 (see FIG. 1). The difference between the ninth embodiment and the first embodiment is the configurations of the data processor 40. FIG. 12 shows an example of the data processor 40 in the ninth embodiment.

The data processor 40J shown in FIG. 12 includes the layer region identifying unit 42J, the front image constructing unit 44J, the blood vessel region extracting unit 41J, the color coding unit 45J, and the image composing unit 46J. Similar to the first embodiment, the three dimensional data set 21 obtained by applying OCT scanning to the subject's eye is stored in the memory 20.

The layer region identifying unit 42J is configured to identify a plurality of layer regions by applying segmentation to the three dimensional data set 21. This process is executed, for example, in the same manner as that executed by the layer region identifying unit in any of the embodiments described above.

The front image constructing unit 44J is configured to construct a front image based on each of the plurality of layer regions identified by the layer region identifying unit 42J. This process is executed, for example, in the same manner as that executed by the front image constructing unit in any of the embodiments described above.

The blood vessel region extracting unit 41J is configured to extract a blood vessel region from each of the plurality of front images constructed by the front image constructing unit 44J. This process is executed, for example, in the same manner as that executed by the blood vessel region extracting unit of any of the embodiments described above. Note that the above-described embodiments are configured to extract a blood vessel region from three dimensional image data. On the other hand, the ninth embodiment is configured to extract a blood vessel region from two dimensional image data (specifically, from a front image). There is no fundamental difference between the image region extraction from three dimensional image data and the image region extraction from two dimensional image data.

The color coding unit 45J is configured to assign mutually different color information to the plurality of blood vessel regions extracted by the blood vessel region extracting unit 41J. This process is executed, for example, in the same manner as that executed by the color coding unit of any of the embodiments described above.

The image composing unit 46J is configured to compose at least two of the plurality of blood vessel regions to which color information has been assigned by the color coding unit 45J, to construct a composite front image. This process is executed, for example, in the same manner as that executed by the image composing unit in any of the embodiments described above.

According to the ophthalmological device of the ninth embodiment configured as described above, a composite front image such as the composite front image $G_{n1+n2}$ illustrated in FIG. 3 can be constructed. Furthermore, the ophthalmological device is capable of displaying a composite front image and incidental information, as illustrated in FIG. 4A and FIG. 4B.

In the ninth embodiment, the memory 20 corresponds to the memory, the layer region identifying unit 42J corresponds to the ninth layer region identifying unit, the front image constructing unit 44J corresponds to the ninth front image constructing unit, the blood vessel region extracting unit 41J corresponds to the ninth blood vessel region extracting unit, the color coding unit 45J corresponds to the ninth color coding unit, and the image composing unit 46J corresponds to the ninth image composing unit. In addition, the display unit 2 corresponds to the display device, and the display controller 11 corresponds to the display controller.

Tenth Embodiment

Figure 13:
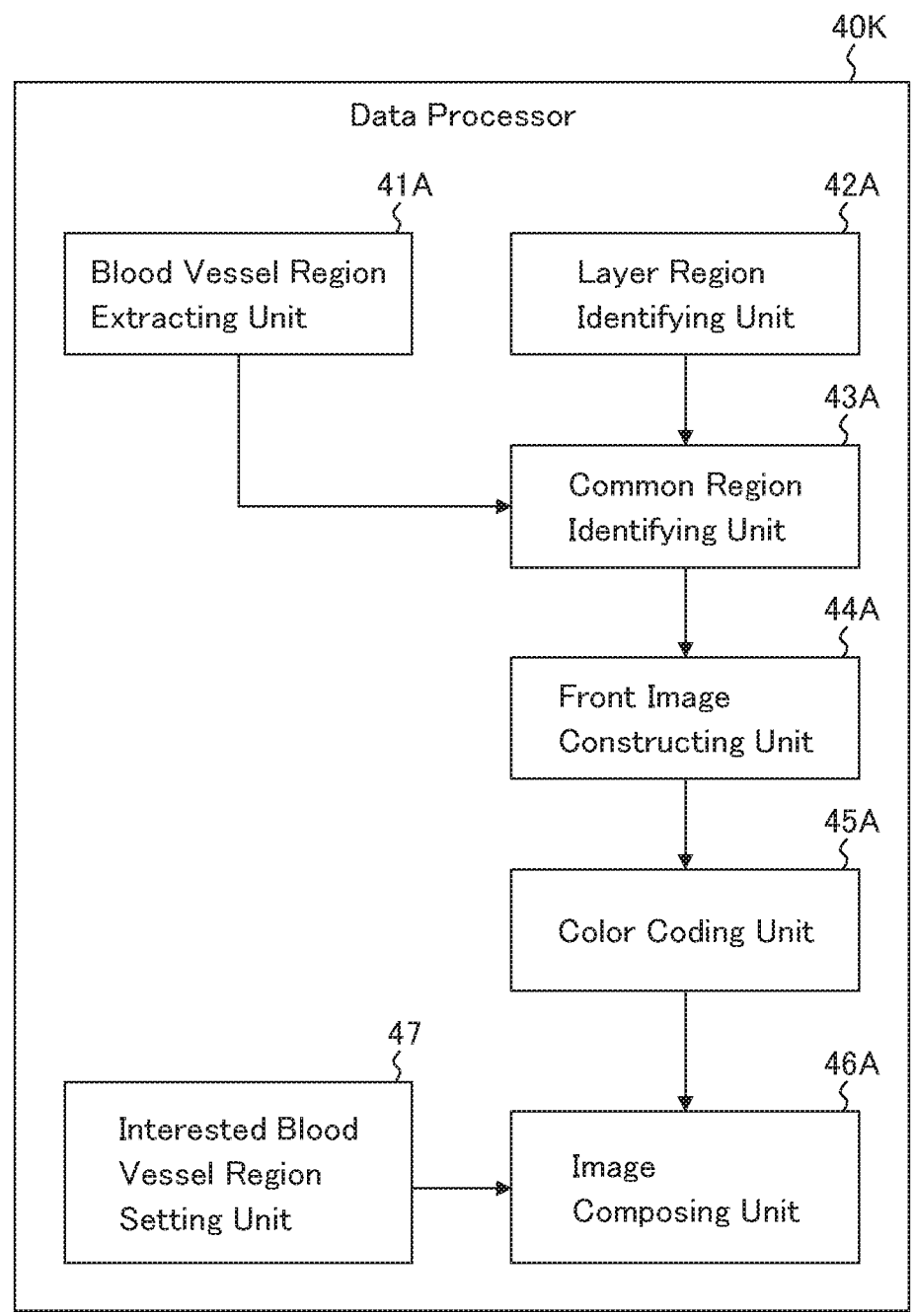
FIG. 13 is a schematic diagram illustrating an example of the configuration of the ophthalmological device according to the exemplary embodiment.

The ophthalmological device according to the tenth embodiment will be described. As in the first embodiment, the ophthalmological device according to the tenth embodiment includes the controller 10, the memory 20, the data input and output unit 30, the data processor 40, and the operation unit 50 (see FIG. 1). The difference between the tenth embodiment and the first embodiment is the configurations of the data processor 40. FIG. 13 shows an example of the data processor 40 in the tenth embodiment.

The data processor 40K shown in FIG. 13 includes the blood vessel region extracting unit 41A, the layer region identifying unit 42A, the common region identifying unit 43A, the front image constructing unit 44A, the color coding unit 45A, and the image composing unit 46A, as in the first embodiment. In addition to these elements, the data processor 40K includes the interested blood vessel region setting unit 47. In other words, the data processor 40K is obtained by combining the interested blood vessel region setting unit 47 with the data processor 40A of the first embodiment.

Note that the interested blood vessel region setting unit 47 may be combined with any of the data processors 40B to 40J. Further, the interested blood vessel region setting unit 47 may also be combined with any embodiment or any aspect other than the data processors 40A to 40J.

The memory 20 of the tenth embodiment stores the three dimensional data set 21 acquired by applying OCT scanning to the subject's eye as in the first embodiment.

In the tenth embodiment, the user may arbitrarily, optionally, freely change depth ranges displayed as a composite front image. More specifically, the user may designate a desired depth range from the whole depth range of the three dimensional data set 21. Here, the whole depth range of the three dimensional data set 21 is the domain of definition in the depth direction. The ophthalmological device of the tenth embodiment may construct a composite front image corresponding to the depth range designated by the user.

Such depth range designation is performed using the operation unit 50. Designating the depth range substantially corresponds to selecting two or more front images from among the plurality of front images constructed by the front image constructing unit 44A.

Some examples of the method of designating the depth range will be described. In the first example, the display controller 11 displays the plurality of front images constructed by the front image constructing unit 44A on the display unit 2 in a parallel or sequential manner. The user may designate two or more desired front images using the operation unit 50. The data processor 40K may construct a composite front image from the two or more front images designated by the user.

In the second example, the display controller 11 displays information indicating the site and/or tissue of the subject's eye on the display unit 2. For example, the display controller 11 displays a list of names of the layer tissues of the eye fundus on the display unit 2. The user can designate two or more desired names from the displayed list. The data processor 40K may identify two or more front images corresponding to the two or more names designated by the user, for example, based on the segmentation result, and then construct a composite front image from the identified two or more front images.

The interested blood vessel region setting unit 47 is configured to set an interested blood vessel region among the blood vessel regions extracted by the blood vessel region extracting unit 41A. An interested blood vessel region is an image region corresponding to a blood vessel that draws interest in observation or analysis. An interested blood vessel region is set manually or automatically.

The display controller 11 displays an image rendered from the three dimensional data set 21, on the display unit 2. The user may designate a desired interested blood vessel region from among the blood vessel regions depicted in the rendered image. The interested blood vessel region designating operation may be, for example, a click operation or a drag operation using a pointing device.

Generally, blood vessels are branched. When the user designates a certain blood vessel region as an interested blood vessel region, the interested blood vessel region setting unit 47 applies region growing that starts from a seed point at a position designated by the user, for example. From this, the entire blood vessel region including the designated position (including the branched blood vessel as well) is identified. The interested blood vessel region setting unit 47 may set part or all of the entire blood vessel identified in this way as a interested blood vessel region. In another example, the user may designate the area of the interested blood vessel region.

The display controller 11 may display, on the display unit 2, a composite image of the following images: a composite front image constructed based on two or more front images selected from the plurality of front images; and an interested blood vessel region(s) depicted in one or more front images different from the two or more front images. An example of processing for realizing such composite image display control will be described below.

The image composing unit 46A constructs a composite front image based on the two or more front images selected from the plurality of front images in the same manner as in any of the embodiments described above.

Further, the image composing unit 46A receives the result of setting the interested blood vessel region from the interested blood vessel region setting unit 47. Then, the image composing unit 46A selects a front image in which the interested blood vessel region set by the interested blood vessel region setting unit 47 is depicted, from among the front images different from the two or more front images used for constructing the composite front image. Such processing may be executed, for example, by referring to the three dimensional coordinate values of the pixels included in the interested blood vessel region and the three dimensional coordinate values of the pixels included in the layer region corresponding to the front image.

According to such processing, one or more front images are selected from among the front images different from the two or more front images used for constructing the composite front image. The one or more front images selected here are referred to as interested front images. The image composing unit 46A changes the pixel values of the blood vessel regions other than the interested blood vessel region in the selected front image to default values (e.g., brightness value=0, R value=G value=B value=0, etc.). These default values are pixel values corresponding to the background of the front image (image frame). Thereby, an interested front image in which only the interested blood vessel region is depicted is obtained.

The image composing unit 46A composes the interested front image in which only the interested blood vessel region is represented and the composite front image based on the two or more front images. The display controller 11 displays the resulting composite image of the interested front image and the composite front image on the display unit 2.

Note that it is not necessary to perform a process of composing the interested front image in which only the interested blood vessel region is depicted and the composite front image based on the two or more front images. If this is the case, for example, the display controller 11 may display the interested front image in which only the interested blood vessel region is depicted and the composite front image based on the two or more front images in an overlapping manner using the layer display function described above. Alternatively, the display controller 11 may display the interested front image and the two or more front images in an overlapping manner using the layer display function.

According to the tenth embodiment as described above, the user can change the depth range displayed as the composite front image. In addition, with regard to the blood vessel of interest, parts other than the depth range of the composite front image may also be observed by the user.

Eleventh Embodiment

The ophthalmological device according to the eleventh embodiment will be described. The ophthalmological device according to the eleventh embodiment has the function of acquiring a three dimensional data set by applying OCT scanning to the subject's eye. In other words, the ophthalmological devices according to the first to tenth embodiments include at least a computer (e.g., hardware such as a processor, and software); however, the ophthalmological device according to the eleventh embodiment is an OCT device that includes at least a computer and an OCT scanner.

Figure 14:
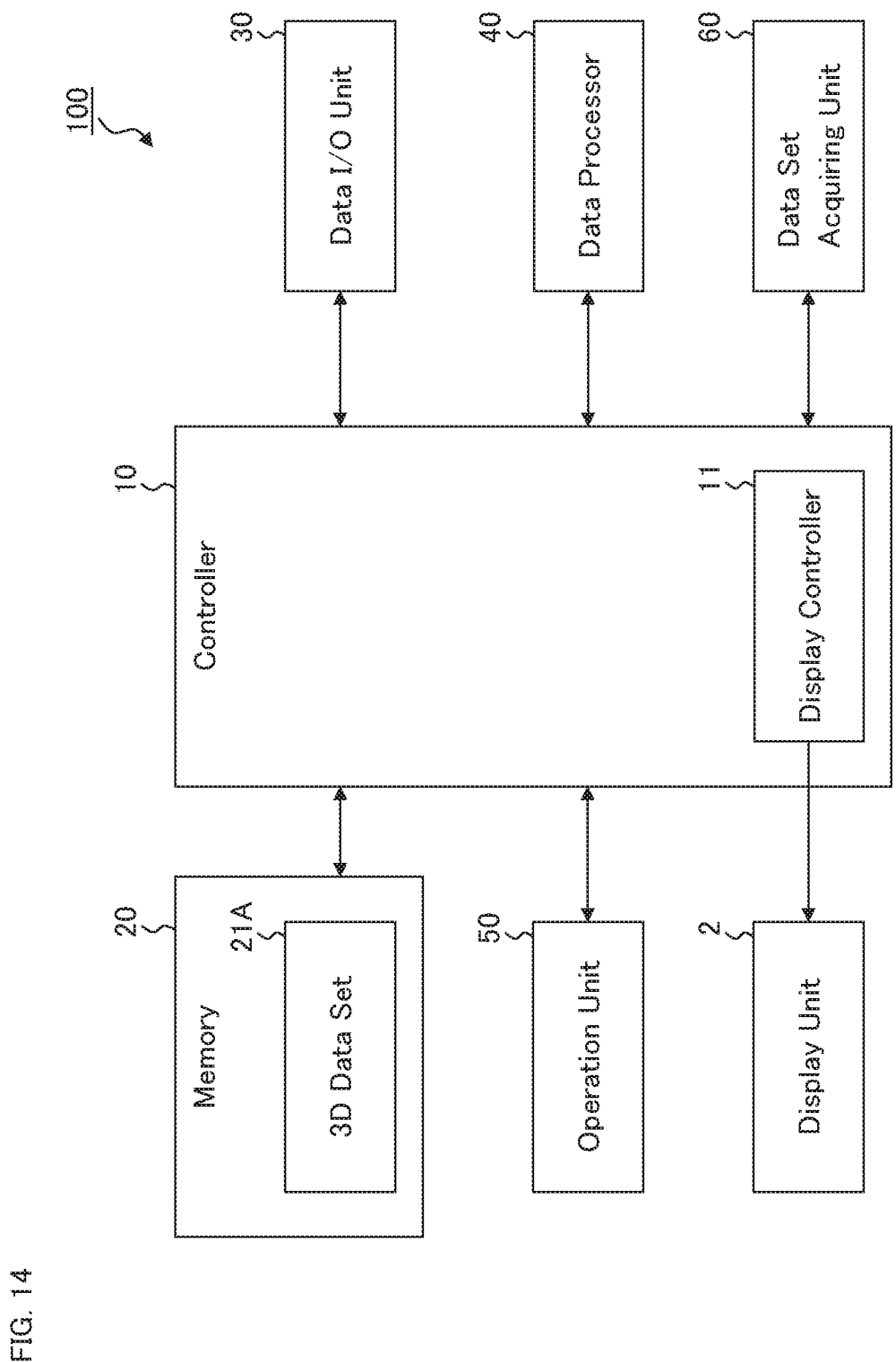
FIG. 14 is a schematic diagram illustrating an example of the configuration of the ophthalmological device according to the exemplary embodiment.

FIG. 14 shows an example of the ophthalmological device according to the eleventh embodiment. The ophthalmological device 100 shown in FIG. 14 includes the controller 10, the memory 20, the data input and output unit 30, the data processor 40, and the operation unit 50, as in the first embodiment (see FIG. 1). In addition to these elements, the ophthalmological device 100 includes the data set acquiring unit 60. Note that, the data processor 40 may be any of the data processors 40A to 40K described above. Alternatively, the data processor 40 may have a configuration other than those of the data processors 40A to 40K.

The data set acquiring unit 60 includes an optical system, a drive system, a control system, and a data processing system for executing OCT scanning. The data set acquiring unit 60 is configured to execute, for example, Fourier domain OCT. The executable Fourier domain OCT may be spectral domain OCT or swept source OCT.

The spectral domain OCT is an OCT technique of acquiring a data set by acquiring a spectrum of interference light in a space division manner using a broadband low coherence light source and a spectroscope, and by applying Fourier transform to the spectrum of the interference light acquired.

The swept source OCT is an OCT technique of acquiring a data set by acquiring a spectrum of interference light in a time division manner using a wavelength swept light source (wavelength tunable light source) and a photodetector (e.g., a balanced photodiode), and by applying Fourier transform to the spectrum of the interference light acquired.

The ophthalmological device 100 may include modalities other than OCT. Examples of such modalities include a fundus camera, a scanning laser ophthalmoscope (SLO), a slit lamp microscope, and an ophthalmological surgical microscope. The ophthalmological device 100 may also include a device used for ophthalmological treatment. An example of the ophthalmological treatment device includes a laser treatment device used for photocoagulation treatment or the like.

The data set acquiring unit 60 acquires a three dimensional data set by performing OCT scanning on the subject's eye. The data set acquiring unit 60 includes the following configurations: a configuration to perform measurement using the spectral domain OCT or the swept source OCT (e.g., an optical system, a drive system, a control system, etc.); and a configuration to construct a three dimensional data set based on the data acquired by OCT scanning. The image data constructing process includes processes such as noise elimination (noise reduction), filtering, Fast Fourier Transform (FFT), and the like, for example, as in the conventional OCT technique.

The data set acquiring unit 60 scans a three dimensional region of the subject's eye. The scan mode at that time is, for example, a raster scan (i.e., a three dimensional scan). The raster scan is executed, for example, to scan each of the plurality of B cross sections a predetermined number of times, that is, to sequentially scan the plurality of B cross sections a predetermined number of times each. The data set acquiring unit 60 constructs a plurality of cross sectional images (B-scan images) for each B cross section based on data acquired by the raster scan. By embedding these cross sectional images in a single three dimensional coordinate system, stack data is constructed. In this stack data, a predetermined number of cross sectional images are assigned to each B cross section. Further, volume data (i.e., voxel data) is constructed by performing interpolation processing and the like on the stack data. For this volume data as well, a predetermined number of voxel groups are assigned to positions corresponding to the respective B cross sections. Stack data and volume data are examples of three dimensional data sets.

The three dimensional data set acquired by the data set acquiring unit 60 is stored in the memory 20 by the controller 10 (the three dimensional data set 21A shown in FIG. 14). The ophthalmological device 100 applies, for example, the processing described in any of the first to tenth embodiments to the three dimensional data set 21A.

Effects

According to the first to eleventh embodiments, the ophthalmological device is capable of extracting blood vessel regions from among image regions of various kinds of tissues depicted in a blood vessel emphasized image, and applying color coding to a composite image (a composite front image) of the extracted blood vessel regions. This makes it possible for the user to grasp the three dimensional distribution of blood vessels in the eye in a clearer manner as compared with the conventional techniques in which tissues other than blood vessels are also depicted.

The configurations, embodiments, and aspects described above are only examples for implementing the present invention. Therefore, any modifications (e.g., omissions, replacements, substitutions, additions) within the scope of the gist of the present invention can be made as appropriate.

What is claimed is:

1. An ophthalmological device comprising:
a memory that stores a three dimensional data set acquired by applying optical coherence tomography to a subject's eye;
a third color coding unit that assigns color information according to a depth position to the three dimensional data set;
a third blood vessel region extracting unit that extracts a blood vessel region from the three dimensional data set;
a third layer region identifying unit that identifies a plurality of layer regions by applying segmentation to the three dimensional data set;
a third common region identifying unit that identifies a common region between the blood vessel region and a layer region, for each of the plurality of layer regions;
a third front image constructing unit that constructs a front image based on each of a plurality of common regions identified by the third common region identifying unit; and
a third image composing unit that composes at least two of a plurality of front images constructed by the third front image constructing unit based on the color information, to construct a composite front image.

2. The ophthalmological device of claim 1, further comprising a display controller that displays the composite front image on a display device based on the color information.

3. The ophthalmological device of claim 2, further comprising an operation unit that receives an operation for selecting two or more front images from among the plurality of front images,
wherein the display controller displays a composite front image constructed based on the two or more front images selected using the operation unit, on the display device.

4. The ophthalmological device of claim 3, further comprising an interested blood vessel region setting unit that sets an interested blood vessel region in the blood vessel region,
wherein the display controller displays a composite image of the composite front image constructed based on the two or more front images and the interested blood vessel region in a front image different from the two or more front images from among the plurality of front images, on the display device.

5. The ophthalmological device of claim 1, further comprising a data set acquiring unit that acquires a three dimensional data set by applying optical coherence tomography to a subject's eye,
wherein the memory stores the three dimensional data set acquired by the data set acquiring unit.

6. An ophthalmological device comprising:
a memory that stores a three dimensional data set acquired by applying optical coherence tomography to a subject's eye;
a fourth color coding unit that assigns color information according to a depth position to the three dimensional data set;
a fourth layer region identifying unit that identifies a plurality of layer regions by applying segmentation to the three dimensional data set;
a fourth blood vessel region extracting unit that extracts a blood vessel region from each of the plurality of layer regions;
a fourth front image constructing unit that constructs a front image based on each of a plurality of blood vessel regions extracted by the fourth blood vessel region extracting unit; and
a fourth image composing unit that composes at least two of a plurality of front images constructed by the fourth front image constructing unit based on the color information, to construct a composite front image.

7. The ophthalmological device of claim 6, further comprising a display controller that displays the composite front image on a display device based on the color information.

8. The ophthalmological device of claim 7, further comprising an operation unit that receives an operation for selecting two or more front images from among the plurality of front images,
wherein the display controller displays a composite front image constructed based on the two or more front images selected using the operation unit, on the display device.

9. The ophthalmological device of claim 8, further comprising an interested blood vessel region setting unit that sets an interested blood vessel region in the blood vessel region,
wherein the display controller displays a composite image of the composite front image constructed based on the two or more front images and the interested blood vessel region in a front image different from the two or more front images from among the plurality of front images, on the display device.

10. The ophthalmological device of claim 6, further comprising a data set acquiring unit that acquires a three dimensional data set by applying optical coherence tomography to a subject's eye,
wherein the memory stores the three dimensional data set acquired by the data set acquiring unit.

11. An ophthalmological device comprising:
a memory that stores a three dimensional data set acquired by applying optical coherence tomography to a subject's eye;
a fifth color coding unit that assigns color information according to a depth position to the three dimensional data set;
a fifth blood vessel region extracting unit that extracts a blood vessel region from the three dimensional data set;
a fifth layer region identifying unit that identifies a plurality of layer regions by applying segmentation to the three dimensional data set;
a fifth common region identifying unit that identifies a common region between the blood vessel region and a layer region, for each of the plurality of layer regions;
a fifth front image constructing unit that constructs a front image based on the color information and a common region, for each of a plurality of common regions identified by the fifth common region identifying unit; and
a fifth image composing unit that composes at least two of a plurality of front images constructed by the fifth front image constructing unit, to construct a composite front image.

12. The ophthalmological device of claim 11 further comprising a display controller that displays the composite front image on a display device based on the color information.

13. The ophthalmological device of claim 12, further comprising an operation unit that receives an operation for selecting two or more front images from among the plurality of front images,
   wherein the display controller displays a composite front image constructed based on the two or more front images selected using the operation unit, on the display device.

14. The ophthalmological device of claim 13, further comprising an interested blood vessel region setting unit that sets an interested blood vessel region in the blood vessel region,
   wherein the display controller displays a composite image of the composite front image constructed based on the two or more front images and the interested blood vessel region in a front image different from the two or more front images from among the plurality of front images, on the display device.

15. The ophthalmological device of claim 11, further comprising a data set acquiring unit that acquires a three dimensional data set by applying optical coherence tomography to a subject's eye,
   wherein the memory stores the three dimensional data set acquired by the data set acquiring unit.

16. An ophthalmological device comprising:
   a memory that stores a three dimensional data set acquired by applying optical coherence tomography to a subject's eye;
   a sixth color coding unit that assigns color information according to a depth position to the three dimensional data set;
   a sixth layer region identifying unit that identifies a plurality of layer regions by applying segmentation to the three dimensional data set;
   a sixth blood vessel region extracting unit that extracts a blood vessel region from each of the plurality of layer regions;
   a sixth front image constructing unit that constructs a front image based on the color information and a blood vessel region, for each of a plurality of blood vessel regions extracted by the sixth blood vessel region extracting unit; and
   a sixth image composing unit that composes at least two of a plurality of front images constructed by the sixth front image constructing unit, to construct a composite front image.

17. The ophthalmological device of claim 16, further comprising a display controller that displays the composite front image on a display device based on the color information.

18. The ophthalmological device of claim 17, further comprising an operation unit that receives an operation for selecting two or more front images from among the plurality of front images,
   wherein the display controller displays a composite front image constructed based on the two or more front images selected using the operation unit, on the display device.

19. The ophthalmological device of claim 18, further comprising an interested blood vessel region setting unit that sets an interested blood vessel region in the blood vessel region,
   wherein the display controller displays a composite image of the composite front image constructed based on the two or more front images and the interested blood vessel region in a front image different from the two or more front images from among the plurality of front images, on the display device.

20. The ophthalmological device of claim 16, further comprising a data set acquiring unit that acquires a three dimensional data set by applying optical coherence tomography to a subject's eye,
   wherein the memory stores the three dimensional data set acquired by the data set acquiring unit.

* * * * *